(12) United States Patent
Yaghoubi et al.

(10) Patent No.: US 12,055,542 B2
(45) Date of Patent: Aug. 6, 2024

(54) SYSTEM AND METHODS FOR REMOTE ASSESSMENT OF A SAMPLE ASSAY FOR DISEASE DIAGNOSTICS

(71) Applicant: Quidel Corporation, San Diego, CA (US)

(72) Inventors: Houman Yaghoubi, San Diego, CA (US); Curtis Marsh, San Diego, CA (US); Scott Rongey, San Diego, CA (US); Ziad Salem, San Diego, CA (US); Adonis Stassinopoulos, Dublin, CA (US)

(73) Assignee: Quidel Corporation, San Diego, CA (US)

( * ) Notice: Subject to any disclaimer, the term of this patent is extended or adjusted under 35 U.S.C. 154(b) by 91 days.

(21) Appl. No.: 17/333,944

(22) Filed: May 28, 2021

(65) Prior Publication Data

US 2021/0373008 A1    Dec. 2, 2021

Related U.S. Application Data

(60) Provisional application No. 63/035,219, filed on Jun. 5, 2020, provisional application No. 63/031,989, filed on May 29, 2020.

(51) Int. Cl.
*G01N 33/543* (2006.01)
*G01N 21/64* (2006.01)
(Continued)

(52) U.S. Cl.
CPC ... *G01N 33/54373* (2013.01); *G01N 21/6428* (2013.01); *G01N 21/6456* (2013.01);
(Continued)

(58) Field of Classification Search
CPC ......... G01N 33/54373; G01N 21/6428; G01N 21/6456; G01N 2021/0118;
(Continued)

(56) References Cited

U.S. PATENT DOCUMENTS 3,092,465 A    6/1963 Adams et al.
6,052,692 A *  4/2000 Anderson ............ H04N 1/2112
                                              707/999.102
(Continued)

FOREIGN PATENT DOCUMENTS

WO    WO 2010/081219 A1    7/2010
WO    WO-2010081219 A1 *  7/2010  ....... G01N 33/48792
(Continued)

OTHER PUBLICATIONS

Saisin et al. "Significant Sensitivity Improvement for Camera-Based Lateral Flow Immunoassay Readers", Sensors, 2018, 18, 4026; doi: 10.3390/s18114026 (from IDS) (Year: 2018).*
(Continued)

*Primary Examiner* — Richard A Hansell, Jr.
(74) *Attorney, Agent, or Firm* — McDermott Will & Emery LLP; Judy M. Mohr; Brennen P. Baylor

(57) ABSTRACT

A circuit in an image-capturing device is provided. The circuit includes a light source controller configured to provide a signal to a light source when a cartridge mount has received, inside a dark chamber, a test cartridge. The circuit also includes a sensor array controller configured to activate at least one pixel in a sensor array when the light source is activated, and to receive a signal from the at least one pixel, the signal indicative of an optical intensity of a light emitted from the test cartridge. The circuit also includes a processor, configured to form a transmittable file with the signal from
(Continued)

the at least one pixel, and a radio-frequency antenna configured to transmit the transmittable file to an external processor.

13 Claims, 30 Drawing Sheets

(51) Int. Cl.
    *H04N 7/18*      (2006.01)
    *H04N 23/56*     (2023.01)
    *H04N 23/62*     (2023.01)
(52) U.S. Cl.
    CPC ............. *H04N 7/183* (2013.01); *H04N 23/56* (2023.01); *H04N 23/62* (2023.01)
(58) Field of Classification Search
    CPC ....... G01N 2201/0256; G01N 21/8483; H04N 5/2256; H04N 5/23216; H04N 7/183
    See application file for complete search history.

(56) References Cited

U.S. PATENT DOCUMENTS

| | | | | |
|---|---|---|---|---|
| 6,833,863 | B1 * | 12/2004 | Clemens | H04N 21/21 |
| | | | | 348/E5.042 |
| D606,664 | S | 12/2009 | Jacono et al. | |
| 9,207,181 | B2 | 12/2015 | Egan et al. | |
| 9,989,466 | B2 | 6/2018 | Booker et al. | |
| 10,168,329 | B2 | 1/2019 | Ren et al. | |
| 10,820,847 | B1 * | 11/2020 | Andeshmand | A61B 5/150961 |
| 2007/0031283 | A1 * | 2/2007 | Davis | A61B 5/15087 |
| | | | | 422/400 |
| 2009/0263854 | A1 | 10/2009 | Jocano et al. | |
| 2010/0028870 | A1 | 2/2010 | Welch et al. | |
| 2011/0194761 | A1 * | 8/2011 | Wang | G06F 16/54 |
| | | | | 382/209 |
| 2012/0224053 | A1 * | 9/2012 | Vykoukal | B01L 3/502715 |
| | | | | 348/135 |
| 2014/0044348 | A1 * | 2/2014 | Chen | G06V 40/16 |
| | | | | 382/159 |
| 2015/0346097 | A1 * | 12/2015 | Battrell | G01N 21/6428 |
| | | | | 702/19 |
| 2016/0349185 | A1 | 12/2016 | Park et al. | |
| 2016/0360124 | A1 * | 12/2016 | Shan | H04N 23/11 |
| 2017/0059566 | A1 | 3/2017 | Reed et al. | |
| 2017/0254804 | A1 | 9/2017 | Cheng | |
| 2017/0337912 | A1 * | 11/2017 | Caligor | H04N 21/4341 |
| 2018/0229232 | A1 | 8/2018 | Chang et al. | |
| 2018/0341818 | A1 * | 11/2018 | Steffanson | G08B 13/19656 |
| 2018/0367469 | A1 * | 12/2018 | Re | G06F 9/468 |
| 2019/0299209 | A1 * | 10/2019 | Dugan | G01N 21/76 |
| 2020/0256856 | A1 | 8/2020 | Chou et al. | |
| 2021/0374959 | A1 | 12/2021 | Yaghoubi et al. | |

FOREIGN PATENT DOCUMENTS

| | | |
|---|---|---|
| WO | WO 2021/243179 A1 | 12/2021 |
| WO | WO 2021/243254 A2 | 12/2021 |

OTHER PUBLICATIONS

Carrio et al., "Automated Low-Cost Smartphone-Based Lateral Flow Saliva Test Reader for Drugs-of-Abuse Detection", Sensors (Basel), vol. 15, No. 11, pp. 29569-29593 (2015).

Foysal et al., "Analyte Quantity Detection from Lateral Flow Assay Using a Smartphone", Sensors, vol. 19, No. 21, Art. 4812, 19 pages (2019).

International Search Report from International Application No. PCT/US2021/034801, 4 pages, Mailed Sep. 13, 2021, application now published as International Publication No. WO2021/243179 on Dec. 2, 2021.

International Search Report from International Application No. PCT/US2021/034928, 5 pages, Mailed Dec. 3, 2021, application now published as International Publication No. WO2021/243254 on Dec. 2, 2021.

Liu et al., "Point-of-care testing based on smartphone: The current state-of-the-art (2017-2018)", Biosens. Bioelectron., vol. 132, pp. 17-37 (2019).

Saisin et al., "Significant Sensitivity Improvement for Camera-Based Lateral Flow Immunoassay Readers", Sensors (Basel), vol. 18, No. 11, Art. 4026, 8 pages (2018).

* cited by examiner 24.5mm working Distance 29.5mm working Distance 37.4mm working Distance

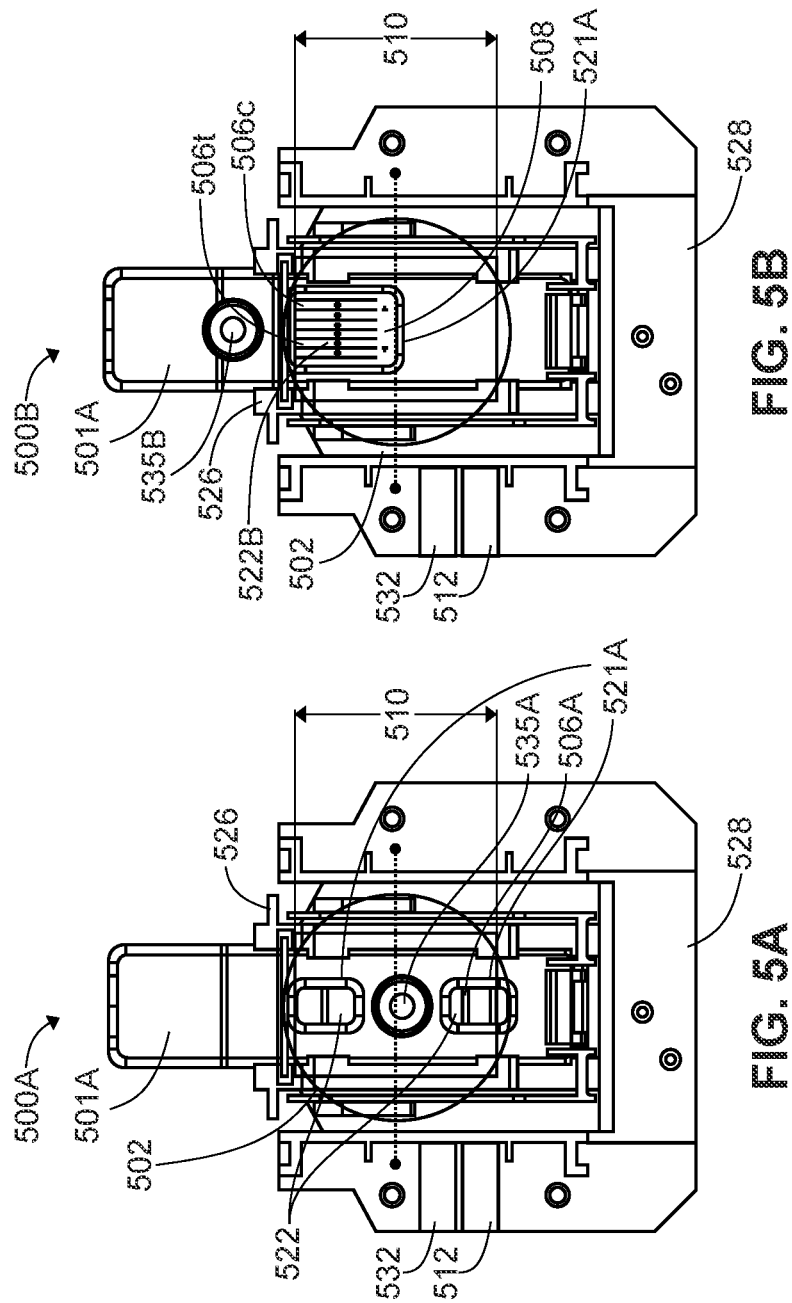

| | VN (internal reference) | |
|---|---|---|
| Power<br>DOV DD: 1.8V<br>AVDD: -0.3V to<br>(VDDIO+1V) | AVDD | |
| | AGND | |
| | DOVDD | |
| | DOGND | |
| PLL<br>Typ: 24MHz<br>Range: 6-27MHZ | XVCLK | ← XVCLK (P1.02) |
| | XSHUTDOWN | |
| Serial Camera<br>Control Bus (SCCB) | SIOD | ← SDA (P1.11) |
| | SIOC | ← SCL (P1.08) |
| Image Interface<br>DVP | D0/SPIVIV0 | — P0.19 → |
| | D1/SPIVIV1 | — P0.20 → |
| | D2/SPI0 | — P0.21 → |
| | D3/SPI1 | — P0.22 → |
| | D4/SPI2 | — P0.23 → |
| | D5/SPI3 | — P0.24 → |
| | D6 | — P0.25 → |
| | D7 | — P0.26 → |
| | PCLK/SPCLK | — P1.15 → |
| | VSYNC/FSIN | — P0.12 → |
| | HREF | — P0.11 → |

Connected to: Nordic

FIG. 12

SYSTEM AND METHODS FOR REMOTE ASSESSMENT OF A SAMPLE ASSAY FOR DISEASE DIAGNOSTICS

CROSS REFERENCE TO RELATED APPLICATIONS

This application claims priority to, and benefit of, U.S. Provisional Application No. 63/035,219, filed Jun. 5, 2020; and U.S. Provisional Application No. 63/031,989, filed May 29, 2020; the entire contents of which are hereby incorporated by reference.

TECHNICAL FIELD

The present disclosure generally relates to devices and methods for home testing, telemedicine applications, and other in-situ immunoassay measurements. More specifically, the present disclosure relates to consumables, which in conjunction with client devices used by consumers may be used in a simple and accurate procedure to assess a disease diagnostic locally and/or remotely.

BACKGROUND

Currently, disease diagnostics using test assays involve users sending test samples to a laboratory for accurate analysis. This step is time-consuming, as it involves the physical displacement of a test cartridge (with the test sample, also referred to as "sample cartridge") back and forth (before use of the test sample) between the medical provider (e.g., clinic, physician, or pharmacy), the laboratory, and the user. Furthermore, these test samples tend to cause delays in clinical laboratories, many times unnecessarily (as many samples may be negative). Further, the time lag between test and result may be a potential hazard, e.g., for epidemic or pandemic emergencies, or when the outcome of treatment of a serious condition is dramatically impacted by the time of start of a therapy, or an infected user leaves the office without an immediate result, neglecting follow up and proceeding to infect others.

BRIEF DESCRIPTION OF THE FIGURES

FIGS. 5A-5C illustrate top-down views of a cartridge mount, with or without a test cartridge in an image-capturing device, the test cartridge including a reading zone delimited by a border, according to some embodiments.

FIG. 12 illustrates a block diagram of an interface between a microcontroller and a sensor array in an image-capturing device, according to some embodiments.

Figure 1:
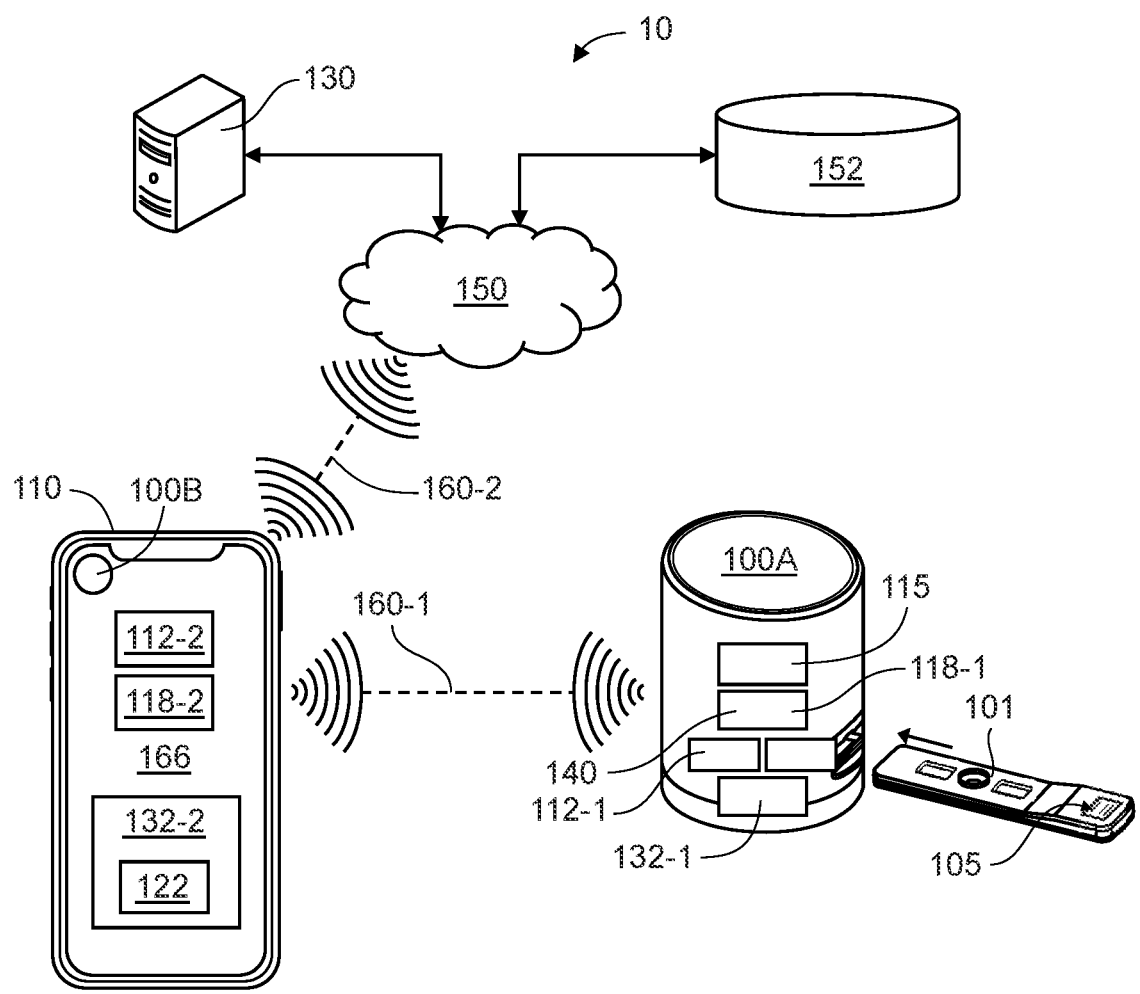
FIG. 1 illustrates an architecture including a remote server, a database, and an image-capturing device to collect an image from a test cartridge in an enclosure, according to some embodiments.

In the figures, features and blocks having same or similar labels have the same or similar description, unless stated otherwise.

DETAILED DESCRIPTION

In the following detailed description, numerous specific details are set forth to provide a full understanding of the present disclosure. It will be apparent, however, to one ordinarily skilled in the art, that the embodiments of the present disclosure may be practiced without some of these specific details. In other instances, well-known structures and techniques have not been shown in detail so as not to obscure the disclosure.

In the burgeoning area of telemedicine, it has become increasingly desirable to take advantage of the almost universal availability of electronic appliances that may have wireless network access and sensors, and that may also include increasingly higher computational capabilities. Moreover, some applications of remote measurement of immunoassays designed for the detection of chemical and biological agents or pathogens may include security tests and screening (e.g., at airports, police and military checkpoints), or environmental analysis and monitoring (e.g., air pollution, contamination of water ways and reservoirs—for disease control or agricultural production—, and the like).

Embodiments consistent with the present disclosure take advantage of the high image-capturing and processing capabilities of current consumer appliances to provide simple yet accurate diagnostic procedures for selected diseases (e.g., legionella, influenza, Ebola, Lyme disease, SARS-Cov2, and the like). The types of tests consistent with embodiments in the present disclosure may include any type of spectroscopic analysis of test assays using electromagnetic radiation, such as, without limitation, absorption spectroscopy (ultra-violet, visible, or infrared), including reflectance or transmittance spectroscopy, or emission spectroscopy, including fluorescence and luminescence spectroscopy, Raman spectroscopy, and any type of radiation scattering. Moreover, embodiments as disclosed herein may further exploit the networking capabilities of such appliances to enhance the processing capabilities of each test by using cloud-computing solutions. Accordingly, in some embodiments, a high quality (e.g., high spatial and spectral resolution) image, sequence of images, or video is uploaded to a remote server that can perform massively parallel computations to provide, in a reduced time, a diagnostic result. Such analyzed material may be processed immediately, at a later date/time, and/or may be compared to previously collected materials to determine differences over time, e.g., a time evolution of the analyte across a test strip. In other cases, the ability to collect and compile data libraries may enable the generation of self-teaching algorithms (Artificial Intelligence or Machine Learning algorithms) from the analysis of such image libraries to generate initial versions and improved versions as the size and diversity of such libraries increases.

The subject system provides several advantages, including the ability for a user to quickly learn whether a disease is present or latent, without the need to access specialized personnel, or a complex machine or instrument.

In some embodiments, the subject system includes an immunodiagnostic analysis system for use with a Fluorescence Immunodiagnostic Assay (FIA) test cartridge. Accordingly, the subject system may include a compact reader device and software residing in a smart phone (as a custom application). Test interpretation may be performed in the phone application, autonomously. In addition, the data and results may be uploaded from the smart phone to a dedicated database.

Some embodiments provide the advantage of widely broadening the market for medical test kits, as consumers who have wide access to mobile computing devices and other appliances may desire to perform tests even before perceiving any symptoms or going to a doctor or clinic. This also may provide the advantage of a screening step before people attend clinics or saturate the resources of a given medical facility. Further, the cost of a test for a remote user of methods as disclosed herein may be substantially lower than the cost associated with a visit to a clinic or laboratory, including waiting times, scheduling, taking an appointment away from a truly infected patient, or exposing a healthy patient to a waiting room full of sick people.

The proposed solution further provides improvements to the functioning of computers (e.g., the server or a user mobile device) because it saves data storage space and interaction time by enabling a remote transmission of image analysis data and results (e.g., pictures, sequences of pictures, and/or videos).

Although many examples provided herein describe a user's personal information and data as being identifiable, or a download and storage of a user interaction history with one or more remote clinics, each user may grant explicit permission for such user information to be shared or stored. The explicit permission may be granted using privacy controls integrated into the disclosed system. Each user may be provided notice that such user information will be shared with explicit consent, and each user may at any time end the information sharing, and may delete any stored user information. Further, in some embodiments, the stored user information may be encrypted to protect user security and identity.

In some embodiments, it is desirable that an image-capturing device as disclosed herein have a useful lifetime greater than two (2) "seasons," with there being four (4) months per season and a utilization rate of three (3) tests per day. Accordingly, the electronic components in embodiments as disclosed herein may be selected to have a durability well within the desired lifetime. In some embodiments, the usage of an image-capturing device as disclosed herein may be selected to be: Greater than several hundred tests (e.g., more than 720 tests in 2 seasons×4 months per season×30 days per month×3 tests per day); Greater than 1,920 hours of operation—assuming the device is left powered on for 8 hours per day; a light source lifetime greater than 1440 seconds (assuming an ultra-violet light emitting diode—UV LED—left 'ON' nominally for 2 seconds for every test).

FIG. 1 illustrates an architecture 10 including a remote server 130, a database 152, a client device 110, and an image-capturing device 100A to collect an image or video from a test cartridge 101, according to some embodiments. In some embodiments, image-capturing device 100A is designed to work with most, or all, of commercially available FIA test cartridges, and can in principle be used with any assay developed on these test cartridges. Client device 110 may include a smartphone or other mobile computing device (e.g., Bluetooth capable device such as, tablet, pad, watch, such as an Apple watch (iWatch™) or similar, or even a laptop). Architecture 10 provides, in real-time, an accurate assessment as to the presence or not of one or more target analytes in a test sample from an assay result. The assay may be run in test cartridge 101, and may include an immunoassay for detecting the one or more analytes of interest in a biological sample. Test cartridge 101 may provide a substrate for flowing the biological sample on multiple test channels for detection of 1-20 analytes of interest (or more). Images of the assay as it progresses may be provided by image-capturing device 100A communicatively coupled with client device 110.

Test cartridge 101, in one embodiment, is an immunoassay test strip enclosed in a housing or cartridge to ease its handling. In other embodiments, test cartridge 101 is simply an immunoassay test strip, such as a dip stick. That is, an external housing is optional, and if present, need not be a cartridge or test cartridge housing but can be a flexible laminate, such as that disclosed in U.S. Patent Application Publication No. 2009/02263854 and shown in Design Patent No. D606664. An immunoassay test strip, in one embodiment, comprises in sequence, a sample pad, a label pad, one or more lines or bands selected from a test line, a control line and a reference line, and an absorbent pad. In some embodiments, a support member is present, and each or some of the sample pad, label pad, lines, and absorbent pad are disposed on the support member. Exemplary immunoassay test strips are described, for example, in U.S. Pat. Nos. 9,207,181, 9,989,466, and 10,168,329 and in U.S. Publication Nos. 2017/0059566 and 2018/0229232, each of which is incorporated by reference herein. Additional details on immunoassay test strips are provided infra.

In some embodiments, the assay is an immunoassay including reagents for detection of an infectious agent (e.g., a virus or a bacterium) in the biological sample. In some embodiments, the immunoassay may include reagents for detection of protein, including antibodies against specific analytes, or a small molecule biomarker or an autoantibody. In some embodiments, the analytes of interest are detectable by emission of a unique signal associated with each analyte selected from the analytes of interest. In some embodiments, the biological sample includes a body fluid (e.g., blood, serum, plasma, sputum, mucus, saliva, tear, feces, or urine). In some embodiments, the biological sample is human and the presence of one or more target analytes may indicate a medical diagnostic for an individual providing the sample. Accordingly, in some embodiments, architecture 10 includes a user of client device 110 who has ordered a kit including test cartridge 101 and image-capturing device 100A and is ready to perform a personal test for a disease or condition remotely from a hospital or clinic (e.g., at home, in a pharmacy, retail store, doctor's office, and the like).

In architecture 10, image-capturing device 100A includes an enclosure 120 to prevent ambient light from perturbing or interfering with the measurement. In some embodiments, image-capturing device 100A wirelessly transmits an image of test cartridge 101 to client device 110. Client device 110 then may transmit the image or video to a remote server 130, to database 152, or both, via network 150, for processing. In some embodiments, image-capturing device 100A and/or client device 110 may perform at least one or more operations to the image or one or more image frames from a video using processors 112-1 and/or 112-2, respectively (hereinafter, collectively referred to as "processors 112"), before transmitting the image to server 130 or to database 152. For example, in some embodiments, client device 110 may perform at least one or more quality control steps over the one or more images provided by image-capturing device 100A before transmitting to server 130. In some embodiments, client device 110 may obtain a preliminary or a definitive diagnostic based on the analysis of the image of test cartridge 101. Accordingly, in some embodiments, client device 110 may transmit the preliminary or definitive diagnostic to server 130 with or without an image of test cartridge 101. To perform their operations, processors 112 may execute instructions and collect or save data, the instructions and data stored in a memory 132-1 (in image-capturing device 100A) or in a memory 132-2 (in client device 110).

Client device 110 communicates with image-capturing device 100A via a signal 160-1 and with server 130 via a signal 160-2, using a communication module 118-2. For example, in some embodiments, signal 160-1 includes a transmittable file generated by processor 112-1, including data from an array sensor collecting an image from test cartridge 101. And signal 160-2 may include a diagnostic of the assay based on image analysis of the transmittable file. Image-capturing device 100A may communicate with client device 110 through a communication module 118-1. Signals 160-1 and 160-2 (hereinafter, collectively referred to as "signals 160") may be digital or analog signals, wireless signals, radiofrequency (RF) signals, electrical signals, Ethernet signals, and the like. Communication modules 118-1 and 118-2 will be collectively referred to, hereinafter, as "communication modules 118." Communication modules 118 may include hardware and software associated with RF antennas for communication via Wi-Fi, Bluetooth (e.g., low energy Bluetooth, BLE), or nearfield contact (NFC) protocols. For example, when image-capturing device 100A and client device 110 are relatively close to each other, communication module 118 may include a BLE or NFC protocol.

In addition, any one of signals 160 may be encrypted and/or encoded for security purposes.

In some embodiments, image-capturing device 100A may include a sensor array 140 and an optics coupling mechanism 115 (e.g., a lens system with or without autofocus capabilities). In some embodiments, optics coupling mechanism 115 is a single lens. In some embodiments, optics coupling mechanism 115 may include diffractive, refractive, and reflective components such as mirrors, prisms, gratings, and the like. In some embodiments, optics coupling mechanism 115 may also include waveguide optical elements, such as semiconductor waveguides, fiber optics, and the like. Sensor array 140 may collect one or more images of test cartridge 101 at a desired frame rate, to form a video. In some embodiments, sensor array 140 may collect a single image of test cartridge 101 (e.g., after an assay has run its course), or more than one image (e.g., before and after an assay runs its course). In yet some embodiments, sensor array 140 may collect multiple images of test cartridge 101 at a pre-selected frequency rate. The frequency rate may be adjusted, modified, accelerated, or slowed, based on preliminary or quality control tests performed by client device 110.

Remote server 130 may provide support for an image-capturing application 122 installed in memory 132-2 of client device 110. The support may include update installation, retrieval of raw data (e.g., pictures, sequences of pictures and videos) for storage in database 152, image processing, and the like. Image-capturing application 122 may include commands and instructions to control image-capturing device 100A. Image-capturing application 122 may also include commands and instructions to perform at least a partial analysis of the one or more images provided by image-capturing device 100A. For example, in some embodiments, the instructions in image-capturing application 122 may include a neural network (NN), artificial intelligence (AI), or a machine learning (ML) algorithm to assess a diagnostic based on the one or more images of test cartridge 101. Additionally, in some embodiments, image-capturing application 122 may include instructions to assess a quality control of the one or more images provided by image-capturing device 100A, based on sensor data indicative of the positioning of test cartridge 101 within enclosure 120. The sensor data may be provided by sensors disposed within enclosure 120.

In some embodiments, client device 110 may further include an image-capturing device 100B to collect an image of a fiduciary label 105 on test cartridge 101. Accordingly, image-capturing application 122 may incorporate the image of a label 105 on test cartridge 101 into a measurement protocol. The measurement protocol may be transmitted by client device 110 to server 130 and/or to database 152, where metadata associated with sampling cartridge 101 may be correlated with information stored therein. For example, in some embodiments, the metadata in fiduciary label 105 may be correlated with a user identifier (ID) and with an assay identification code (e.g., flu test, Lyme disease test, pregnancy test, hepatitis, or any other disease or assay). Hereinafter, image-capturing devices 100A and 100B will be collectively referred to as "image-capturing devices 100."

In some embodiments, image-capturing application 122 may also include instructions for the user as to the mode of use and a measurement protocol for test cartridge 101. For example, the instructions may illustrate to the user, step by step, how to collect a sample (e.g., using a swab or other extraction mechanism), mix the sample with appropriate reagents, and provide at least a portion of the sample into test cartridge 101. Accordingly, image-capturing application 122 may display the instructions and other illustrative icons to the user on a display 116 of client device 110.

Figure 2:
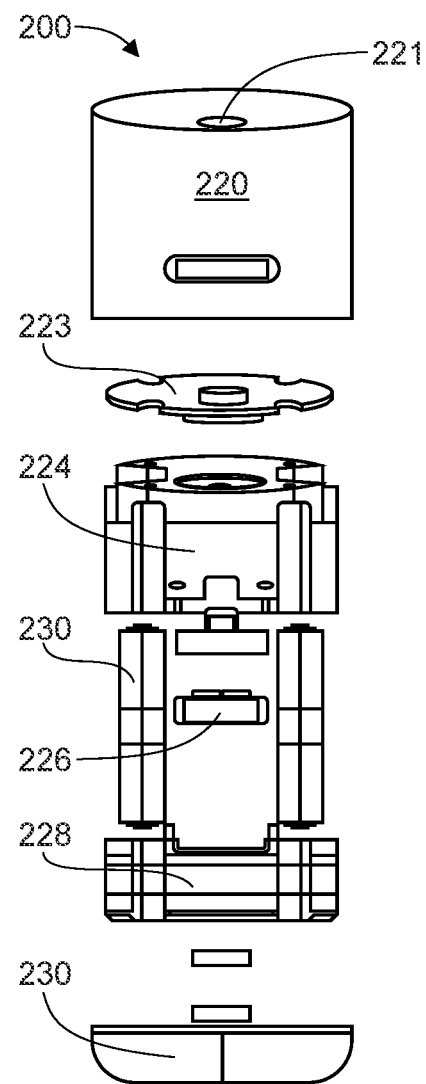
FIG. 2 illustrates an enclosure and other internal components in an image-capturing device, according to some embodiments.

FIG. 2 illustrates an enclosure 220, and other internal or external components in an image-capturing device 200, according to some embodiments. Enclosure 220 serves as a light-tight element covering a circuit support board 223 disposed over an optical chassis 224 and a cartridge mount 226. In some embodiments, the image-capturing device 200 includes a light indicator 221 on top of enclosure 220. The light indicator 221 provides user feedback related to the image-capturing device 200 stage and progress of image collection. For example, in some embodiments, light indicator 221 changes from one color to another, and or from flashing to solid in order to provide user feedback on the progress of the assay. In some embodiments, for example, light indicator 221 comprises a light emitting diode (LED) that changes color and from flashing to solid to indicate stage and progress of assay. In some embodiments, light indicator 221 may comprise three different colors and two patterns (e.g., solid and blinking). For example, light indictor 221 may cycle through blue blinking, blue solid, red blinking, red solid, purple blinking, purple solid, to indicate a status or stage change of the instrument. In some embodiments, a blinking blue indicator light 221 may inform the user that the image-capturing device is plugged in, a solid blue indicator light 221 may inform the user that the image-capturing device is connected to a device, such as paired to a smartphone, a blinking red indicator light 221 may inform the user that the image-capturing device is ready to receive a test cartridge, a blinking purple indicator light 221 may inform the user that the assay is in progress, a solid purple indicator light 221 may inform the user that the assay is complete and results delivered to the connected device.

With further reference to FIG. 2, cartridge mount 226 receives a test cartridge (e.g., test cartridge 101). Circuit support board 223 may include a sensor array, the sensor array disposed at the image plane of an optics coupling mechanism mounted on optical chassis 224 (e.g., optics coupling mechanism 115). The optics coupling mechanism may display an image of the test cartridge on the sensor array. A base member 228 may support enclosure 220 and cartridge mount 226. In some embodiments, spacers 230 may be disposed on base member 228 to support optical chassis 224 and adjust a distance between the optics coupling mechanism and the test cartridge in cartridge mount 226, accordingly.

FIGS. 3A-3D illustrate an optical chassis 324 and a cartridge mount 326 in an image-capturing device 300, according to some embodiments.

Figure 3A:
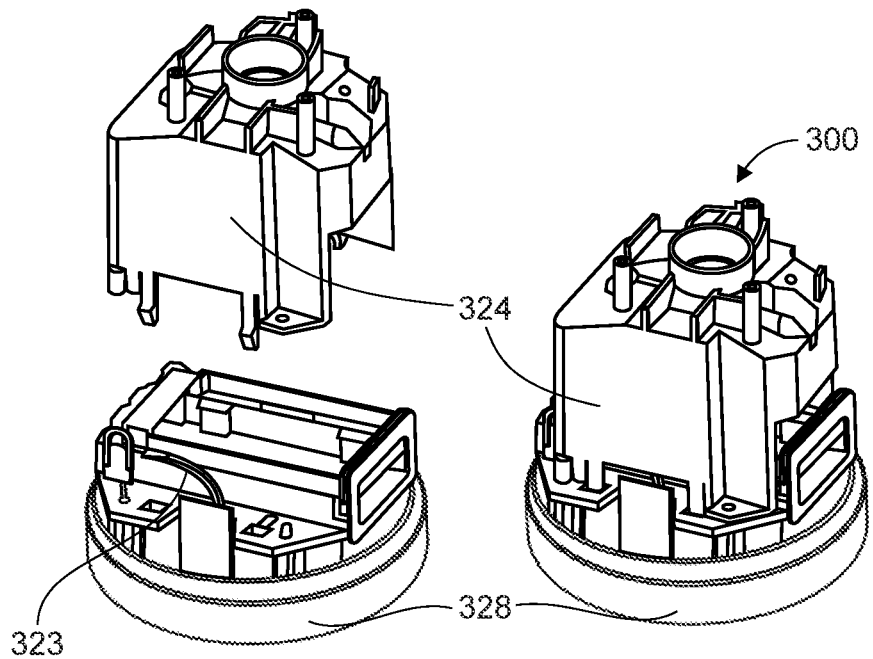
FIGS. 3A-3D illustrate an optical chassis and a cartridge mount in an image-capturing device, according to some embodiments.

FIG. 3A illustrates a base member 328 that supports optical chassis 324 and cartridge mount 326. Cartridge mount 326 may include a cam lever 323 that secures the test cartridge in place and closes a light shield thereupon to prevent any ambient light from disrupting a measurement.

Figure 3B:
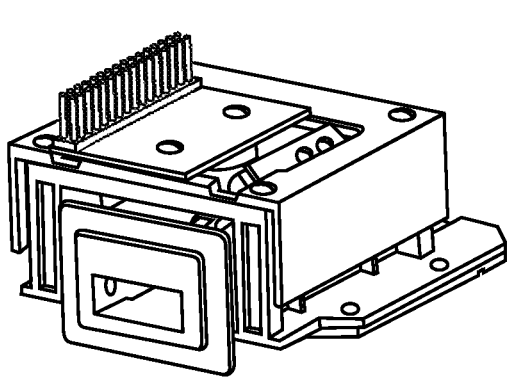
Figure 3C:
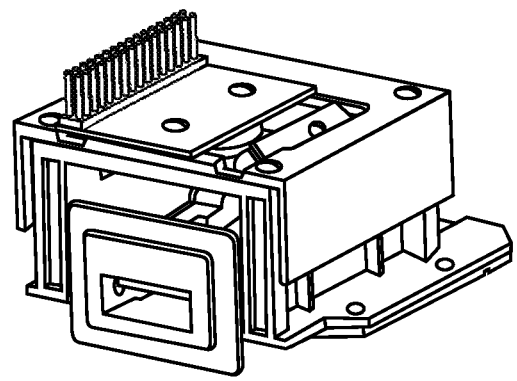
Figure 3D:
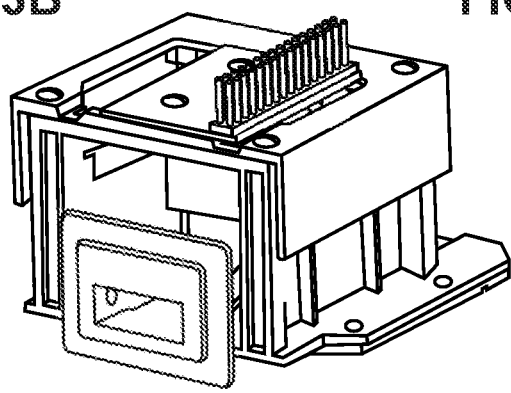

FIGS. 3B-3D illustrate different configurations of the optical chassis according to a selected working distance for the optical setup. The working distance (WD) is the distance between a camera lens and the test cartridge being imaged. In some embodiments, it is desirable to have a shorter working distance for a compact overall design of the enclosure (reduced form factor). In some embodiments, a trade-off occurs between a short working distance and a lower numerical aperture optical system that supports less lens aberration and better image quality. It is understood that FIGS. 3B-3D are exemplary embodiments for illustration purposes only, and other form factors and WDs may be envisioned within the scope of the present disclosure.

FIG. 3B illustrates an optical chassis including a cartridge mount configured for a 24.5 mm working distance.

FIG. 3C illustrates an optical chassis including a cartridge mount configured for a 29.5 mm working distance.

FIG. 3D illustrates an optical chassis including a cartridge mount configured for a 37.4 mm working distance.

FIGS. 4A-4F illustrate a cross sectional view of an enclosure 420, a cartridge mount 426, an optical chassis 424, and a sensor array 440 in image-capturing devices 400A, 400B, 400C, 400D, 400E, and 400F (hereinafter, collectively referred to as "image-capturing devices 400"), according to some embodiments. While FIGS. 4A-4F illustrate specific embodiments, it is understood that different versions of the same components may be leveraged for commercial evaluation kits, or optimized for size and cost, as desired. Some of the components in image-capturing device 400 may be selected as follows:

Sensor Array (Camera)—A Complementary Metal Oxide Semiconductor (CMOS) color sensor (e.g., OmniVision part #: OV07676-H20A) may be selected to capture dark and light images of the test cartridge. In some embodiments, a lens and a UV cutoff filter (580 nm-650 nm) may be attached to the camera to ensure that only the appropriate emission wavelength light is detected.

Light Source—One, two, or more UV LEDs (e.g., Lite-On Inc. part #: LTPL-C034UVH365(OG)) may be selected for the uniform illumination of the test window of the test cartridge. In some embodiments, the UV LEDs may operate with a current of about 500 mA to produce an optical power of about 665 mW, at a wavelength of about 365 nm. In some embodiments, the light sources used to illuminate the test cartridge may include two opposed UV LEDs (e.g., for excitation of Europium-based fluorescent compounds) aligned to provide uniform illumination across a defined imaging area in the test cartridge. In some embodiments, the light source includes a UV LED having an operating life of greater than 1,000 hours. The below table provides various exemplary test conditions. In methods and measurement protocols as disclosed herein, the active operational time of the light source may be only a few seconds per test (as it may be only enabled during a light image capture). Accordingly, the operating conditions in a real case scenario may be substantially less demanding than the test conditions in the below table. Assuming an extreme case wherein the UV LED is let ON for 10 seconds per test (e.g., 5× the expected duration in a regular test)—this equates to just 2 hours of ON time of the UV LED for the desired lifetime of the image-capturing device (~two seasons). Exemplary UV LED Lifetime Test Data is provided in Table 1.

TABLE 1

Exemplary UV LED Lifetime Test Data

| No | Test item | Condition | Duration | Number of Failed |
|---|---|---|---|---|
| 1 | Low Temperature Operating Life (LTOL) | Tc = −10° C., IF = 500 mA DC | 1K hours | 0/10 |
| 2 | Room Temperature Operating Life (RTOL) | 25° C., IF = 700 mA | 1K hours | 0/10 |
| 3 | High Temperature Operating Life (HTOL) | Tc = 85° C., IF = 60 mA DC | 1K hours | 0/10 |
| 4 | Wet High Temperature Operating Life (WHTOL) | 60° C./90° C. % RH, IF = 350 mA | 500 hours | 0/10 |

UV cutoff filters (one, two, or more, typically one for each light source) used to select the wavelength of the light exciting the test cartridge, with a pass band between about 450 nm and 650 nm (e.g., Schott Inc. Part #: UG1 FUG-112).

A System-On-Chip (SoC) is a single integrated circuit (IC) that may be selected as the embedded microprocessor including a Bluetooth radio for the image-capturing device (e.g., Nordic Semiconductor part #: nRF52840-QIAA). In some embodiments, the custom embedded software for operating the image-capturing device may reside within the SoC. The SoC may include a 32-bit embedded processor, with a 64 MHz clock and 1 MB of flash memory, and 256 kB of random access memory—RAM—(e.g., ARM® Cortex®-M4). The SoC may include a Bluetooth radio with a 2.4 GHz transceiver having a 103 dBm sensitivity and up to +8 dBm transmit power that is IEEE 802.15.4-2006 compliant.

Optical Chassis—In some embodiments, the optical chassis is a custom plastic part that determines the distance between the sensor array and the test cartridge in the Z direction (e.g., vertical). This distance may include a working distance between the test cartridge and the lens, and a focal distance between the lens and the sensor array. Accordingly, the shape and dimensions of the optical chassis select a desired optical field of view (FOV) and a desired illumination profile on the supported test cartridge. Furthermore, the optical chassis defines a position and a relative orientation of the one or more light sources versus a region of interest (ROI) in the test cartridge.

A light shield may be a custom plastic part that blocks any ambient light from entering the instrument once a test cartridge has been inserted.

Table 2 computes mean time between failure (MTBF) for the electronic components, according to some embodiments.

TABLE 2

Exemplary Electrical Component Lifetime

|  | Failure Rate per 10^9 hours | Number of Components | Failure Rate |
|---|---|---|---|
| Resistors | 0.008 | 15 | 0.12 |
| Capacitors | 0.004 | 25 | 0.1 |
| Inductors | 0.008 | 4 | 0.032 |
| Transistors | 0.0015 | 3 | 0.0045 |
| BT Chip | 36 | 1 | 36 |
| Camera 1.8 V | 0.1 | 1 | 0.1 |
| Temperature Sensor | 3.4 | 1 | 3.4 |
| CMOS | 50 | 1 | 50 |
| Camera 2.8 V | 0.1 | 1 | 0.1 |
| UV LED Drivers | 5 | 2 | 10 |
| Crystal Oscillator A | 2 | 1 | 2 |
| Crystal Oscillator B | 2 | 1 | 2 |
|  |  |  | 103.86 |
| Mean Time Between Failures (MTBF)-hours: |  |  | 9628670 |

While the choice of electronic components is not limiting, the above table illustrates that many different selections may fall well within the desired operational lifetime of an image-capturing device as disclosed herein.

Figure 4A:
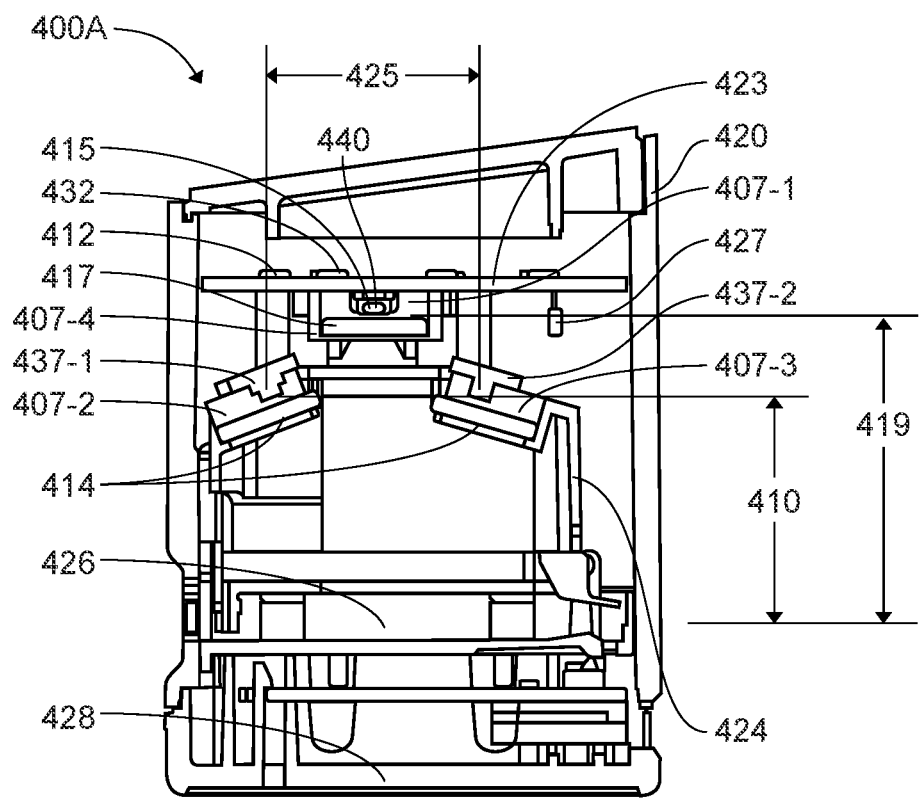
FIGS. 4A-4F illustrate a cross sectional view of an enclosure, a cartridge mount, an optical chassis, and a sensor array in an image-capturing device, according to some embodiments.

FIG. 4A illustrates enclosure 420 configured to block ambient light from entering the dark chamber wherein sensor array 440 and optical chassis 424 are located. Cartridge mount 426 receives a test cartridge to be disposed at least partially inside the dark chamber within enclosure 420. A base member 428 receives and supports cartridge mount 426, optical chassis 424, and enclosure 420.

Optical chassis 426 includes a lens mount 407-1 and at least one light source mount 407-2 and 407-3 at a pre-determined position relative to one another. In some embodiments, sensor array 440 is disposed on an image plane of a lens 415 mounted in lens mount 407-1. In some embodiments, optical chassis 426 further includes at least one filter mount 407-4 for a filter 417 in an optical path between the cartridge mount and the lens mount. Lens mount 407-1, light source mounts 407-2 and 407-3, and filter mount 407-4 will be collectively referred to, hereinafter, as "optical mounts 407." In some embodiments, lens 415 may be a video camera lens, or a smartphone lens.

In some embodiments, image-capturing device 400A includes a memory circuit for storing instructions which, when executed by a processor circuit 412, causes image-capturing device 400A to execute at least partially some of the steps in methods consistent with this disclosure. In some embodiments, processor circuit 412 includes a light source controller configured to provide a signal to one or both of light sources 437-1 and 437-2 (hereinafter, collectively referred to as "light sources 437") when cartridge mount 426 has received a test cartridge inside the dark chamber formed by enclosure 420. Processor circuit 412 may also include a sensor array controller to activate at least one pixel in sensor array 440 when at least one of light sources 437 is 'on.' The sensor array controller in processor circuit 412 also receives a signal from the at least one pixel, the signal indicative of an optical intensity of a light emitted from the test cartridge (e.g., in response to an illumination light provided by either one of light sources 437).

In some embodiments, processor 412 executes instructions to crop a selected area of interest in the test cartridge, and to generate a transmittable file including an image of the area of interest in the test cartridge. In some embodiments, processor 412 executes instructions to encode the transmittable file in a digital format according to a Bluetooth or a Wi-Fi protocol. For example, in some embodiments, processor 412 executes instructions to encrypt the transmittable file according to a security protocol in one of a BLE, Wi-Fi, or any other digital communication configuration. Accordingly, in some embodiments, processor 412 also provides instructions to an RF antenna to transmit the transmittable file to an external processor through an antenna.

In some embodiments, lens mount 407-1 is positioned to define a fixed vertical distance 419 between lens 415 and a reading zone on the test cartridge, a fixed vertical distance 410 between light sources 437 and the reading zone on the test cartridge, and a fixed horizontal distance 425 between light sources 437. In some embodiments, a screw 427 or any other mechanical actuator may adjust distance 419 by acting on a board 423. Board 423 may support processor circuit 412, memory circuit 432, and lens mount 407-4.

In some embodiments, optical mounts 407 are movable relative to each other to adjust a quality of the image of the test cartridge collected by sensor array 440. In some embodiments, processor circuit 412 also includes a processor to activate at least one of optical mounts 407 to adjust a relative position between light sources 437, the test cartridge, and sensor array 440 when the signal from the at least one pixel is less than the pre-determined value. Accordingly, in some embodiments, processor circuit 412 may perform an auto-focus operation and move optical mounts 407 relative to each other to ensure that a sharp image of the test cartridge is collected in sensor array 440. The auto-focus operation may include adjusting a distance 419 between lens 415 and the test cartridge in cartridge mount 426. In some embodiments, moving optical mounts 407 relative to each other may include adjusting an angle 414 between two or more of light sources 437.

Figure 4B:
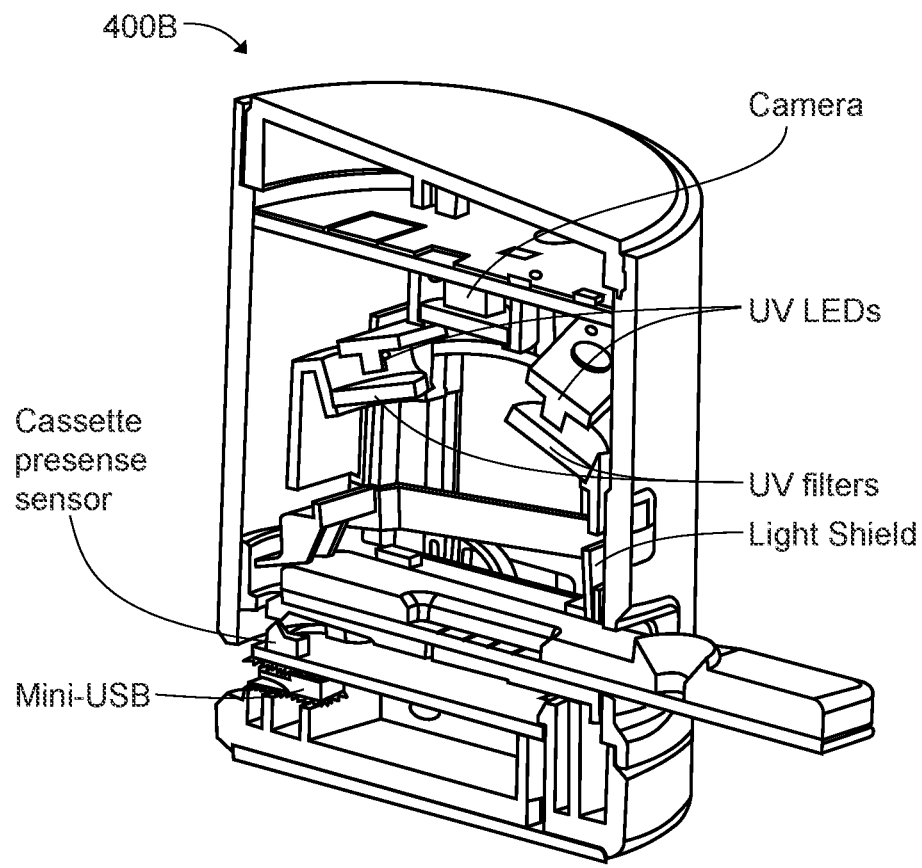

FIG. 4B illustrates a cutout of an enclosure in an image-capturing device 400B, according to some embodiments. A presence sensor to detect the presence of a test cartridge within the enclosure may include a mechanical switch that actuates once a test cartridge has been inserted. In some embodiments, a switch may include an arm that is pushed in the same horizontal axis on which the test cartridge slides in (e.g., Omron Electronics Inc. part number #: SS-10GL13, or TE Connectivity part #: JJEVOUG380NOHPMRTR). In some embodiments, the switch may actuate in the vertical direction (Z-axis) and is depressed when the test cartridge slides over it. The specific selection of the presence sensor may reduce the overall diameter of the enclosure to a desired size. In some embodiments, a USB-C compliant receptacle serves as a power entry for image-capturing device 400B. Accordingly, in some embodiments, image-capturing device 400B internally generates all voltages from the single 5V USB power input.

Image-capturing device 400B also includes a digital temperature sensor to measure the temperature within the optical chamber (e.g., Texas Instruments part #: LMTO1LPGM). In some embodiments, image-capturing device 400B may also include an LED driver to provide a constant current (e.g., from about 60 mA to about 600 mA, or more) to each of the UV LEDs, operating at 12V direct current—dc—(e.g., MikroElektronika part #: MIKROE-3399), or at 5 Vdc (e.g., Diodes Incorporated part #: AL5802-7).

Figure 4C:
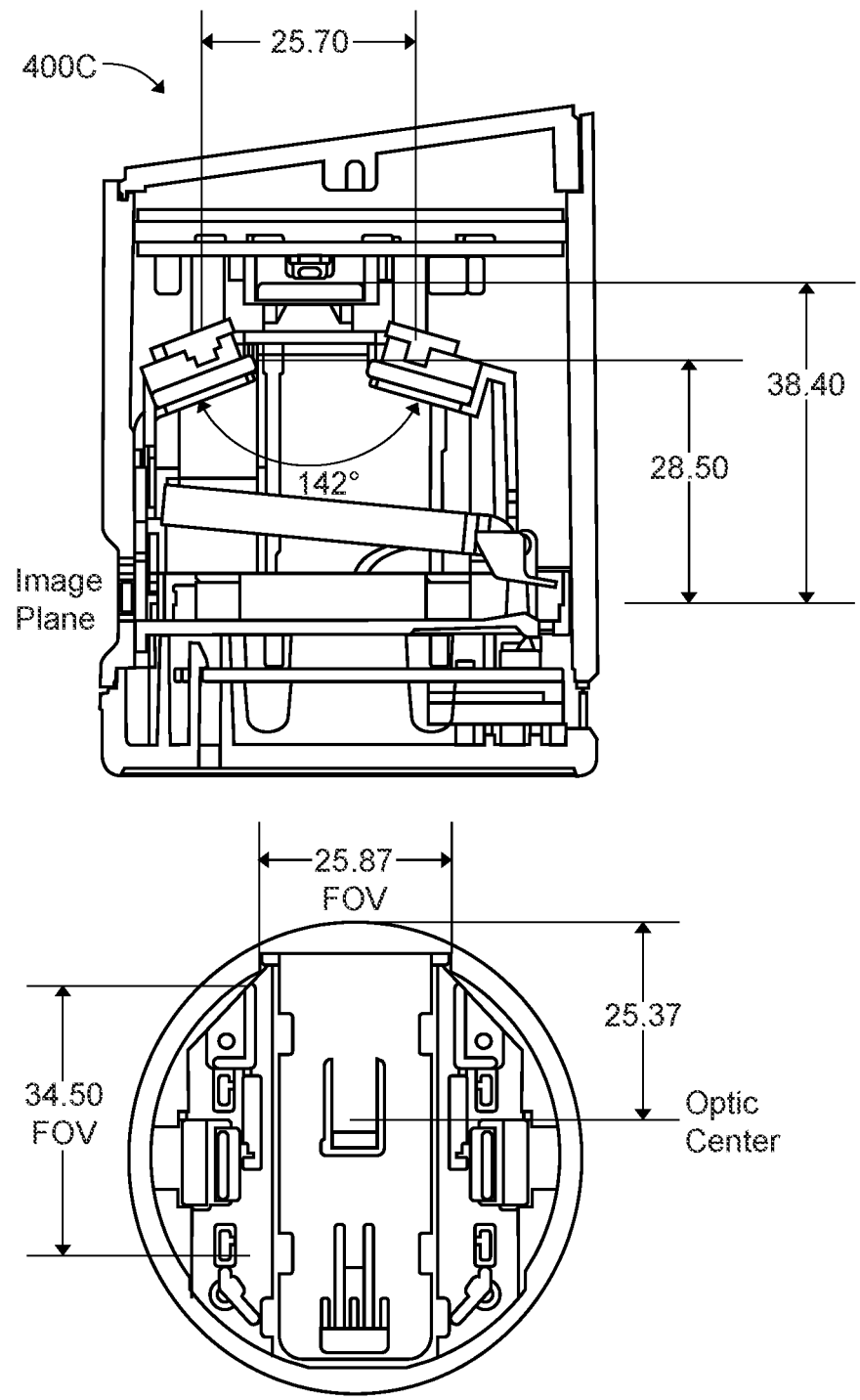

FIG. 4C illustrates a cross section of the enclosure for image-capturing device 400C and a field of view within the enclosure, according to some embodiments. Image-capturing device 400C includes outer dimensions as: 2.3 inches (58.4 mm) in diameter by 3.2 inches (81.3 mm) in height. The receptacle slot is 0.18 inches×0.80 inches (4.9 mm×20.3 mm) to accommodate various commercially available FIA test cartridges.

Figure 4D:
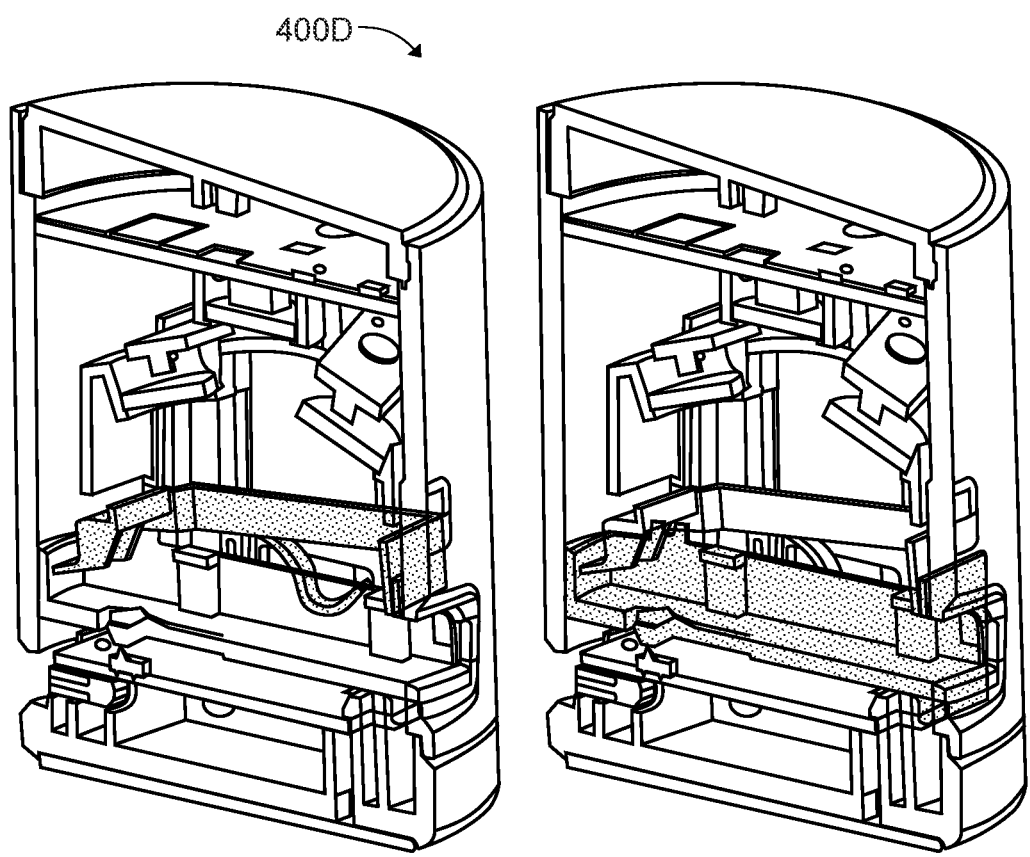

FIG. 4D illustrates a perspective view of an enclosure in image-capturing device 400D, showing the cartridge mount, according to some embodiments. Placing the LEDs along the longitudinal dimension of the test cartridge as in image-capturing devices 400A, 400B, 400C, and 400D avoids shadowing artifacts near the test cartridge sample area. In such embodiments, the optical chassis disposes the light sources at the proximal and distal end of the test cartridge.

Figure 4E:
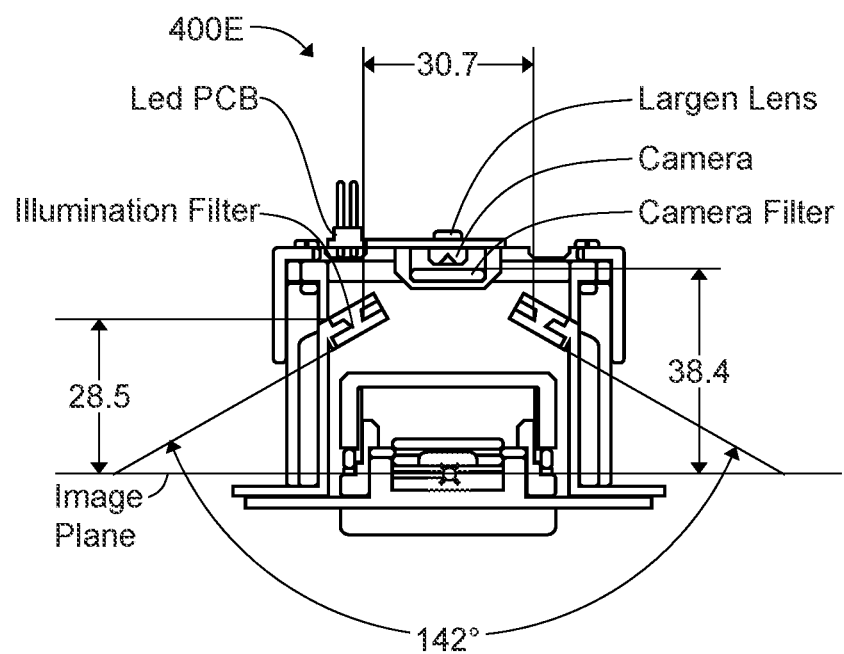

FIG. 4E illustrates a configuration for the different optical components within an enclosure in image-capturing device 400E, according to some embodiments. A light shield shutter is activated by the cam lever when the test cartridge is fully inserted. It remains open to allow test cartridge to pass through. In some embodiments, a lower Printed Circuit Board (PCB) that contains the SoC has a limit switch located so that a lever will activate it when the cartridge is inserted into the receptacle slot. In image-capturing device 400E, the light sources are located along the sides of the test cartridge, and although shadowing effects may be considered, such configurations may allow a more compact design and brighter illumination of test cartridge 401.

Figure 4F:
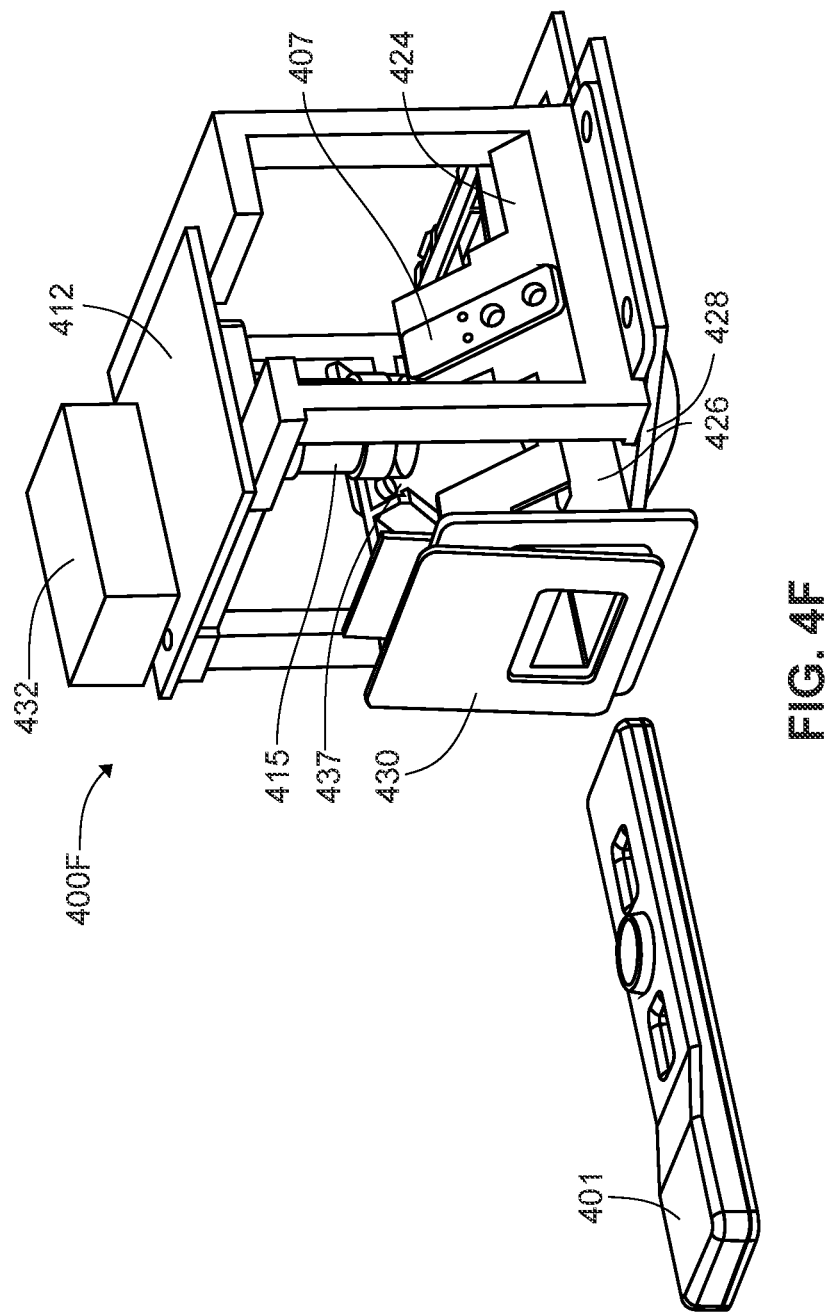

FIG. 4F illustrates a perspective view of an optical chassis 424 and a cartridge mount 426 with a light shield 430 in an image-capturing device 400F, according to some embodiments. In image-capturing device 400F, the light sources are located along the sides of the test cartridge. Test cartridge 401 is inserted into a cartridge mount 426 disposed on base member 428. A light shield 430 is in an open position when cartridge mount 426 is empty. Optical mounts 407 support a light source 437. An optical coupling mechanism 415 provides a partial image of test cartridge 401 to a sensor array controlled by a processor circuit 412 executing instructions stored in a memory circuit 432.

FIGS. 5A-5B illustrate top-down views of a test cartridge 501A and 501B (hereinafter, collectively referred to as "test cartridges 501") inside a cartridge mount 526 in a base member 528, and a field of view 502 of a lens in an image-capturing device 500A and 500B (hereinafter, collectively referred to as "image-capturing devices 500"), respectively. In some embodiments, test cartridges 501 include a reading zone (e.g., reading zones 522A or 522B, hereinafter, collectively referred to as "reading zones 522"), delimited by a border (e.g., 521A and 521B, hereinafter, collectively referred to as "borders 521"). In some embodiments, reading zones 522 are part of a sensitive area of test cartridges 501 having a dimension 510 within field of view 502.

FIG. 5A illustrates a sample collection port 535A in the middle of test cartridge 501A, and two reading zones 522A symmetrically placed adjacent to it.

FIG. 5B illustrates a sample collection port 535B on one end of test cartridge 501B and a reading zone 522B disposed on one side of it. Hereinafter, collection ports 535A and 535B will be referred to as "collection ports 535."

In some embodiments, image-capturing devices 500 include a memory circuit 532 and a processor circuit 512. Memory circuit 532 may store instructions which, when executed by processor circuit 512, causes image-capturing devices 500 to apply a geometrical transformation on the area delimited by borders 521 to bring an image of reading zones 522 to a selected size and a selected shape. In some embodiments, processor circuit 512 executes instructions to identify a target region within reading zones 522 and evaluate a quality of the image based on a size and a dynamic range of the target region. Further, in some embodiments, processor circuit 512 executes instructions to adjust an optical coupling in image-capturing devices 500 when the quality of the image is lower than a selected threshold. In some embodiments, processor circuit 512 executes instructions to find borders 521 and to apply a geometrical transformation on an area delimited by borders 521. In some embodiments, when a quality of the image is greater than the selected threshold, processor circuit 512 determines a subject diagnostic based on a digital analysis of the image. In some embodiments, processor circuit 512 identifies a fiduciary label 508 in the image collected from test cartridges 501. In some embodiments, processor circuit 512 identifies at least test lines 506t and control lines 506c in reading zones 522.

Figure 5C:
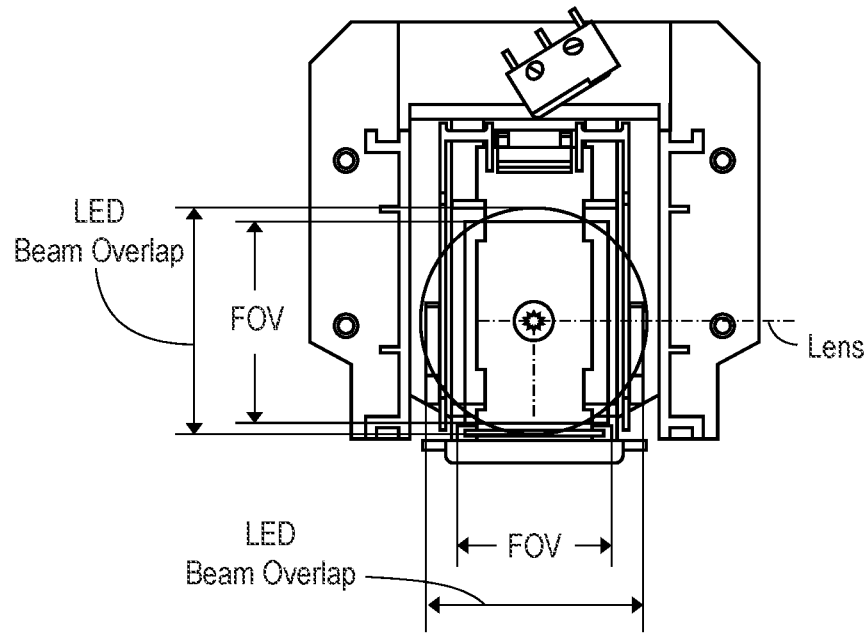

FIG. 5C illustrates top-down views of a cartridge mount without a test cartridge to illustrate the FOV of the optical coupling mechanism (e.g., a camera lens) in an image-capturing device, according to some embodiments. While the specific dimensions are illustrative only, in some embodiments it is desirable that the illumination area generated by the light source be larger than the FOV of the optical coupling mechanism to take maximum advantage of the sensor array.

Figure 6A:
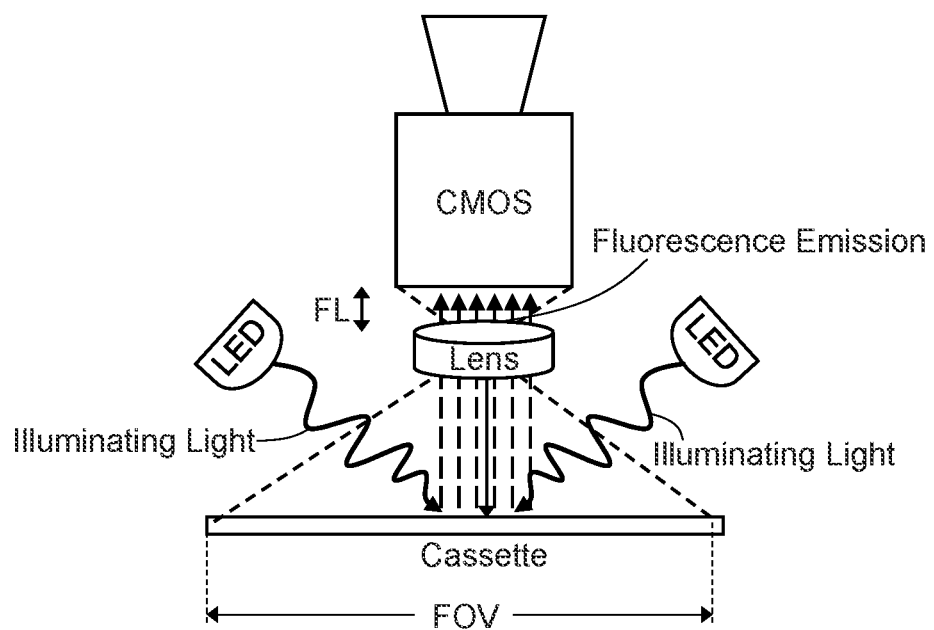
FIGS. 6A-6C illustrate a general layout of the optical components and cross sectional views of an illumination pattern formed over a test cartridge in an image-capturing device, according to some embodiments.

FIG. 6A illustrates a general layout of the optical components and cross sectional views of an illumination pattern formed over a test cartridge in an image-capturing device, according to some embodiments. A focal length (FL) defines the distance between the optics coupling mechanism (e.g., lens) and the sensor array (e.g., a CMOS array, or 'camera') on the image plane of the optics coupling mechanism. A working distance (WD) defines the distance between the optics coupling mechanism and the object to be imaged (e.g., a sensitive area in a test cartridge). An FOV defines the area (e.g., test window) that can be imaged by the optics coupling mechanism on the senor array. In some embodiments, two light sources (e.g., UV LEDs, see above) illuminate the sensitive area in opposite directions to provide a bright, uniform illumination over the test window. The illuminating light excites a fluorescence emission from target compounds captured in the sensitive area of the test cartridge. The fluorescence emission is imaged onto the sensor array.

Figure 6B:
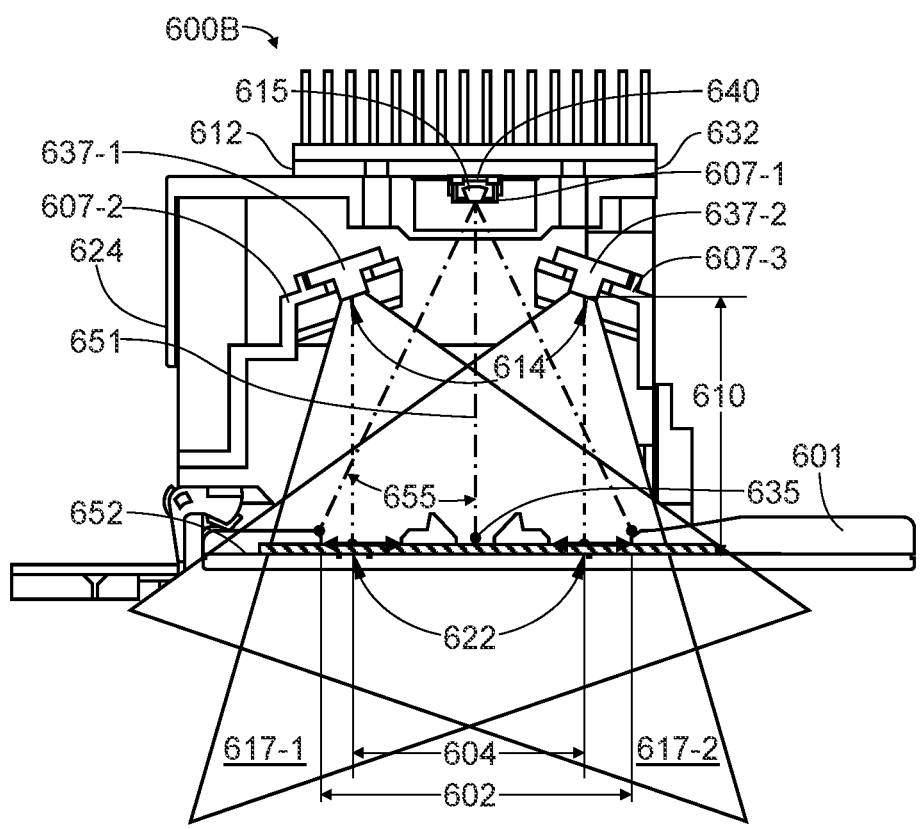

FIG. 6B illustrates a cross sectional view of an illumination pattern formed over a test cartridge 601 by two light sources 637-1 and 637-2 (hereinafter, collectively referred to as "light sources 637") mounted on an optical chassis 624 in an image-capturing device 600B, according to some embodiments. A lens 615 is supported on a lens mount 607-1, and light sources 637 are supported on light source mounts 607-2 and 607-3 (hereinafter, collectively referred to as "optical mounts 607"), respectively. Optical mounts 607 are disposed so that light sources 637 direct illumination lights 617-1 and 617-2 (hereinafter, collectively referred to as "illumination lights 617") respectively, to reading zones 622 on test cartridge 601. In some embodiments, illumination lights 617 impinge on reading zones 622 at an angle 655 relative to an optical axis 651 defined by a lens 615 in lens mount 607-1 in a plane, including a longitudinal direction 652 of test cartridge 601. A processor circuit 612 and a memory circuit 632 are coupled to a sensor array 640, as described above (cf. processor circuit 412 and memory circuit 432).

In some embodiments, lens mount 607-1 is positioned to define a field of view 602 for lens 615. Field of view 602 may accommodate multiple reading zones 622. A vertical distance 610 between light sources 637 and reading zones 622, and an angle 614 between the optical axes of each of light sources 637-1 and 637-2 may increase or decrease the field of view 602, among other parameters. Without limitation, in the configuration for image-capturing device 600B, test cartridge 601 includes reading zones 622 separated by a sample collection port 635 over a horizontal distance 604.

Figure 6C:
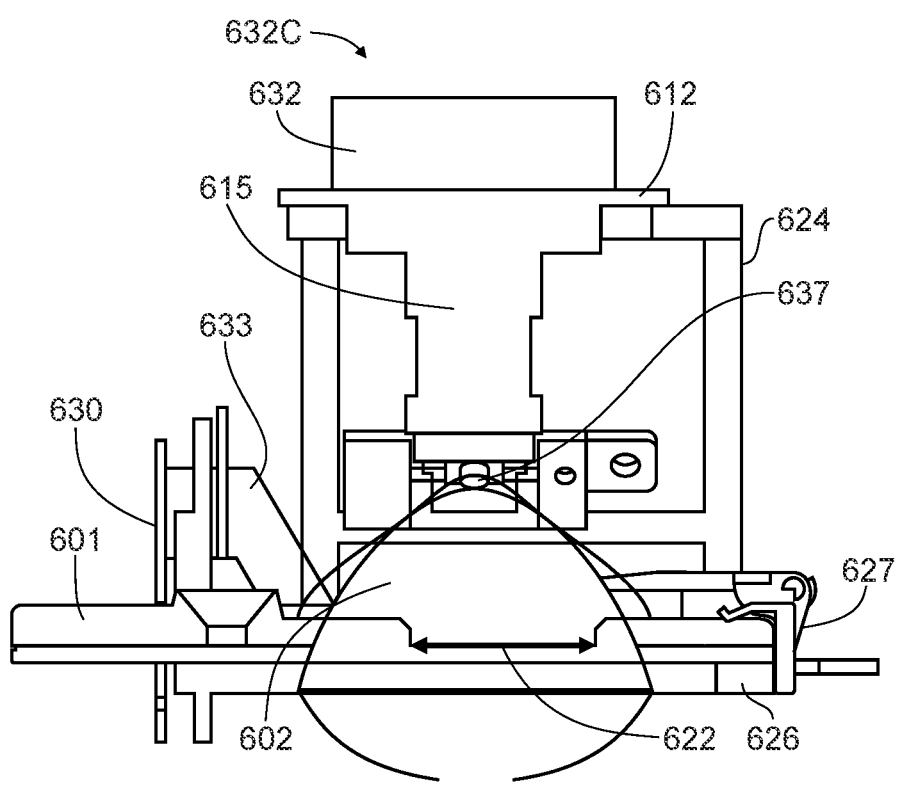

FIG. 6C illustrates a cross sectional view of an illumination pattern formed by light source 637 over test cartridge 601 in image-capturing device 600C, including a field of view 602, according to some embodiments. Hereinafter, devices 600B and 600C will be collectively referred to as "devices 600." Illumination pattern 602 includes a reading zone 622 in test cartridge 601, as it is inserted in cartridge mount 626. When test cartridge 601 is fully seated, a door actuation lever 627 is activated, and cam lever 633 is biased down towards test cartridge 601. Cam lever 633 thus closes light shield 630 in the proximal end of test cartridge 601 and creates a light tight enclosure within optical chassis 624. Optical coupling mechanism 615 provides a partial image of test cartridge 601 to the sensor array controlled by processor circuit 612 executing instructions stored in memory circuit 632.

Figure 7A:
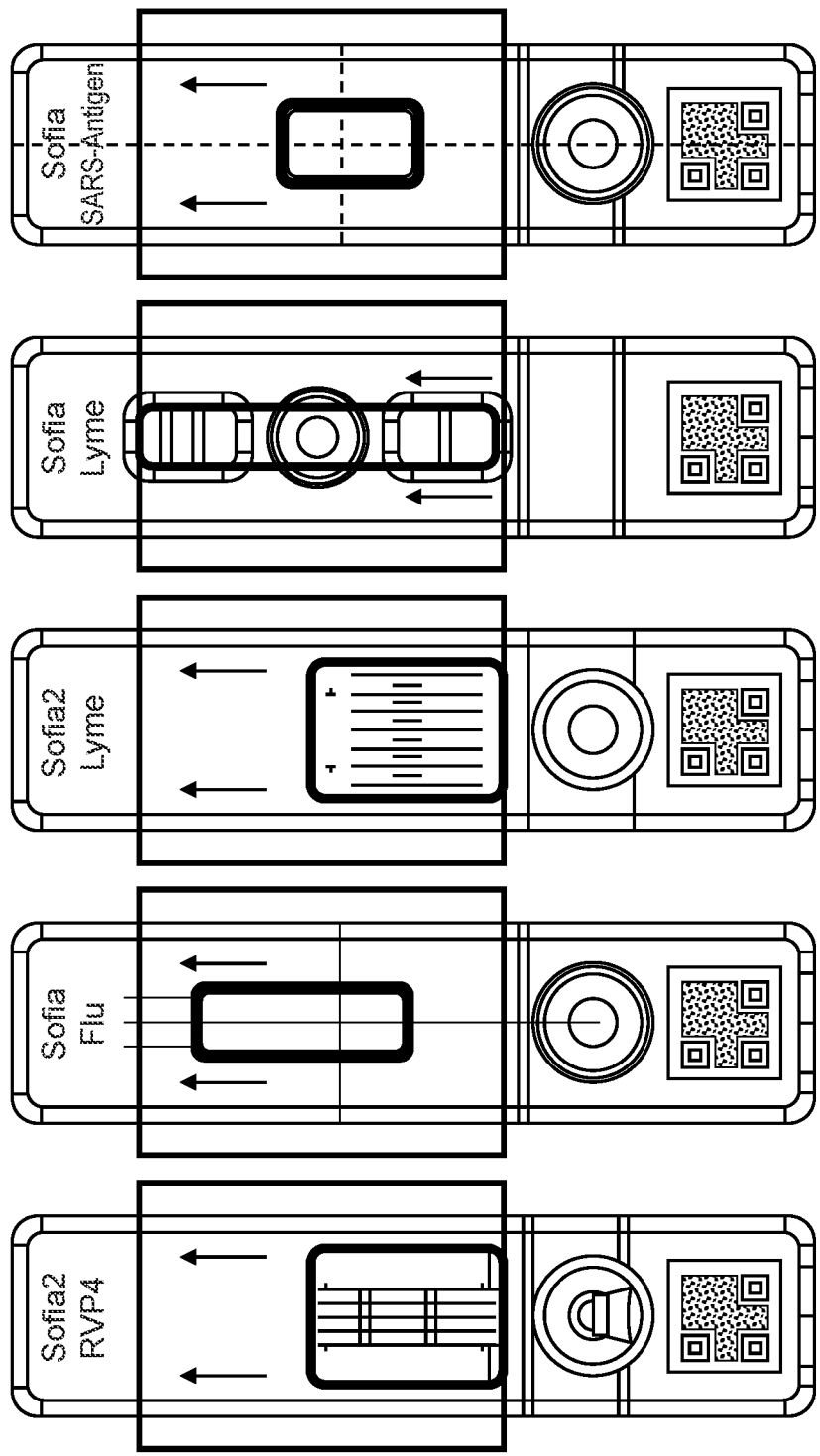
FIGS. 7A-7E illustrate different designs and models for test cartridges for use in an image-capturing device, according to some embodiments.

FIGS. 7A-7E illustrate different designs and models for test cartridges for use in an image-capturing device, according to some embodiments. In some embodiments, the optical chassis may be designed to optimize performance for multiple commercially available test cartridges. Multiple commercially available test cartridges have identical, or similar, overall dimensions. However, the test windows are located in various positions and have different sizes. Accordingly, the optical chassis is configured to provide an illumination area and an FOV for the optics coupling mechanism to encompass different types and sizes of test windows (sensitive areas) for different test cartridge models. In addition, different test cartridge models have test widows in different locations within the test cartridge. The optical chassis also provides homogenous illumination to the illumination area. Some of the test cartridge types to be supported include:

FIG. 7A illustrates that design of the optical chamber has been optimized so that the regions of interest (ROI) for various test cartridges, such as an immunoassay sold under the SOFIA or SOFIA2 tradename (Quidel Corporation), may be accommodated. For example, test cartridges having ROIs indicated by the smaller rectangles encompassing test windows in FIG. 7A which all fall within the field of view (FOV) indicated by the larger rectangle in FIG. 7A. In some embodiments, a FOV rectangle with dimensions of 34.5 mm by 25.9 mm can capture the ROI for supported cassettes.

FIG. 7A illustrates two configurations of a test cartridge (test windows 19.5×5.0 mm and 17.5×12.2 mm, respectively) for detection of an analyte, such as influenza A and/or B, and a test cartridge for detection of an analyte, such as an antigen associated with Lyme disease (test window 34.5×9.8 mm), on the right.

Figure 7B:
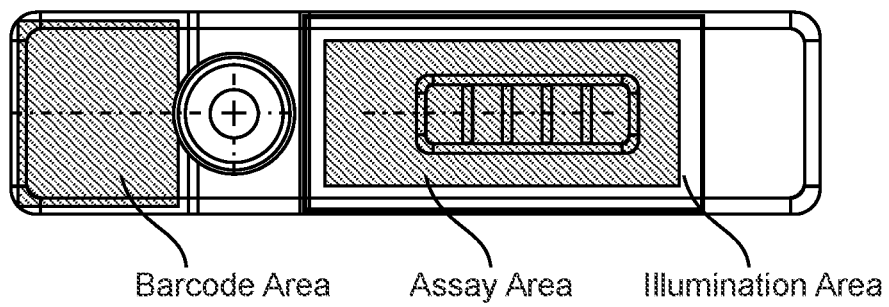

FIG. 7B illustrates a view of different elements of interest for image capturing on a test cartridge, including a barcode area, an assay area, and an illumination area (41×19 mm). A proposed FOV may be approximately rectangular with dimensions 38×15 mm.

Figure 7C:
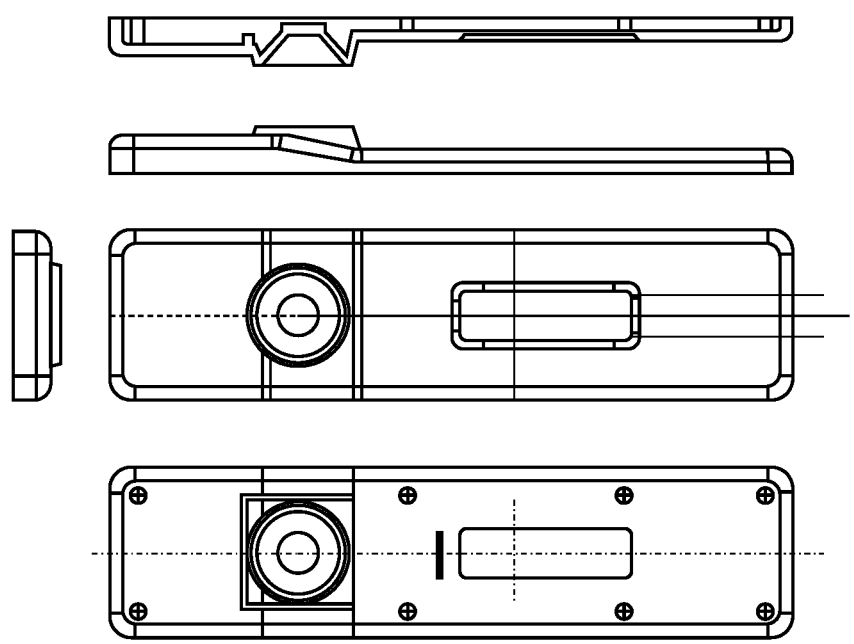

FIG. 7C illustrates a test cartridge for detection of an infection analyte, such as influenza A, B or both.

Figure 7D:
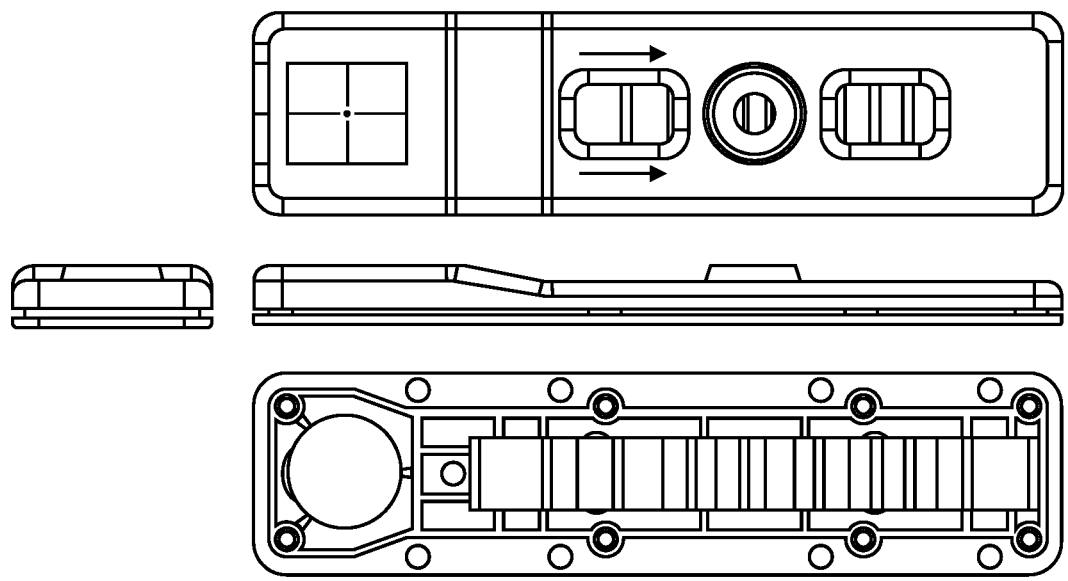

FIG. 7D illustrates a test cartridge, where the sample is collected in a central portion, and two different test assays are run in opposite directions towards two different test windows, each indicative of different analyte components in the sample, including a control assay. In an embodiment, the test cartridge detects, for example, IgG immunoglobulins.

Figure 7E:
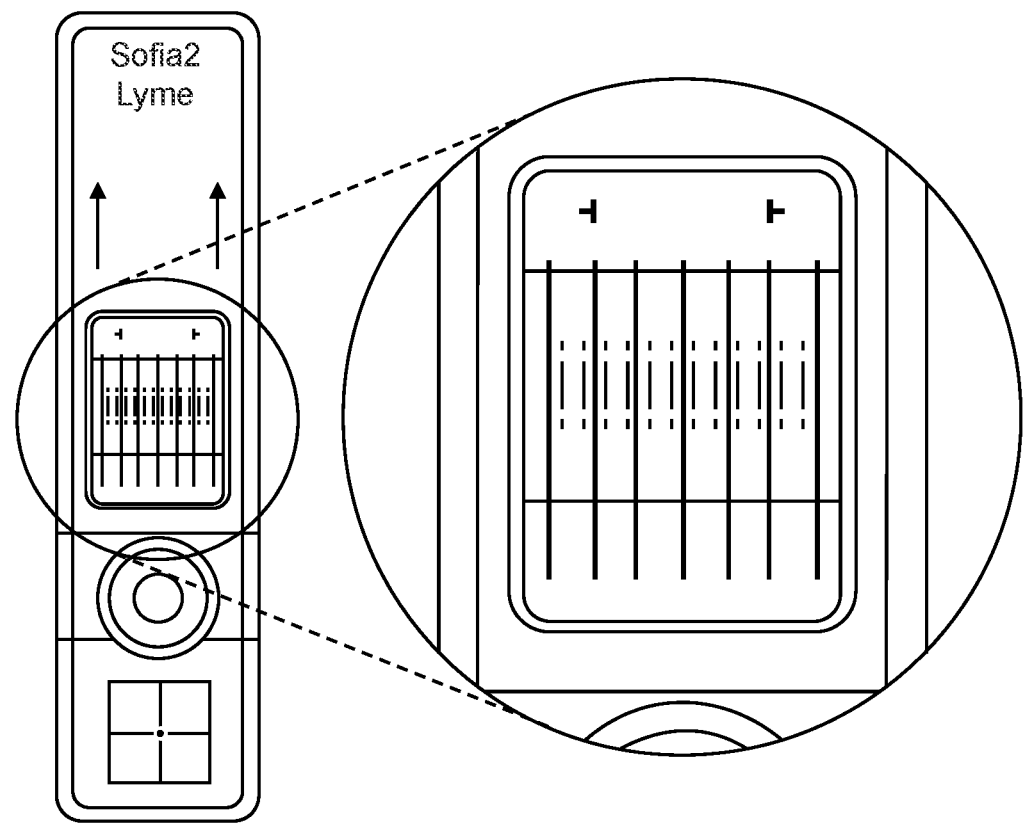

FIG. 7E illustrates a test cartridge including twelve (12) assay lines, to detect up to twelve different target analytes, including control assays.

Figure 8A:
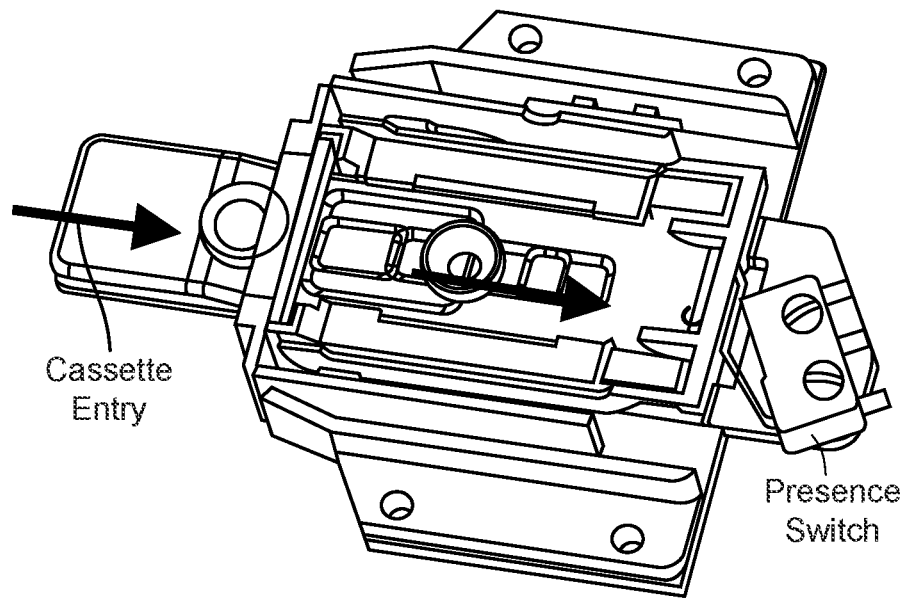
FIGS. 8A-8B illustrate a test cartridge receptacle including a presence sensor in an image-capturing device, according to some embodiments.
Figure 8B:
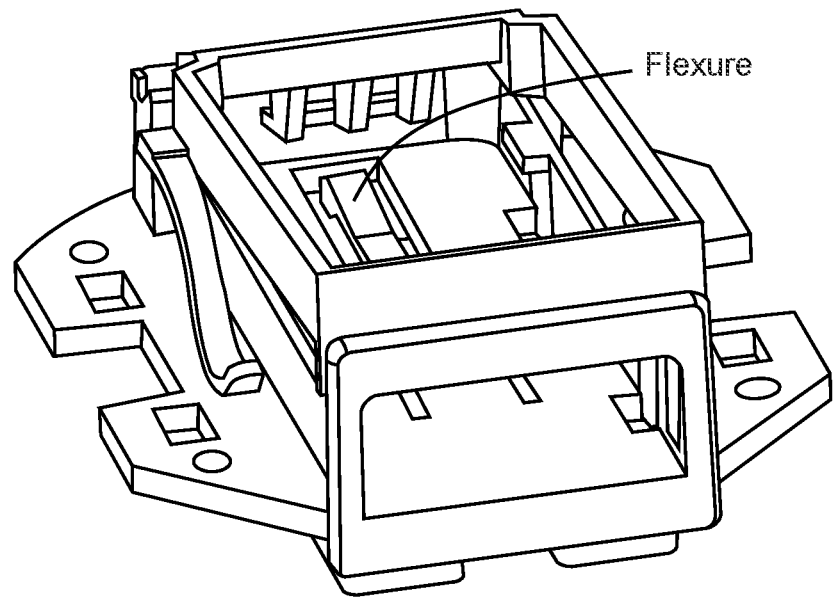

FIGS. 8A-8B illustrate a cartridge mount including a presence sensor in an image-capturing device, according to some embodiments. Some embodiments include features such as: support for multiple types of test cartridges; a test cartridge insertion detector; provide consistent location in the XY direction for the sample window of a given test cartridge; and to block ambient light from entering the instrument during image capture.

FIG. 8A illustrates an embodiment of the cartridge mount configured to produce a consistent position of each inserted test cartridge. In some embodiments, the cartridge mount may receive the test cartridge with maximum width available from multiple commercially available test cartridges. The cartridge mount may include four angular top guide bars, which are molded in the receptacle guide path. These guides contact the top outer side edges of the test cartridge, ensuring that the test cartridge is flat against the bottom inner surface, centrally located. Accordingly, the user may insert the test cartridge until it stops against the rear wall located at the distal end of the cartridge mount.

The cartridge mount also includes a mechanical switch, activated when the test cartridge is fully inserted to detect the test cartridge presence. Some embodiments may include a lever arm switch that is pushed along the same direction as the test cartridge entry. Additionally, an alternate solution was needed to meet the overall diameter requirements for the product version. For the final product design, a lever located in the bottom surface of the receptacle is flexed as the test cartridge is inserted in place, which activates the presence switch. This tells the SoC that there is a test cartridge in the cartridge mount, and will allow the image-capturing device to activate, potentially after a defined time interval.

In some embodiments, the cartridge mount incorporates a light shield to block ambient light. This may be desirable in embodiments configured to accept a bidirectional test cartridge that has two discrete fluid flow paths (e.g., for Lyme disease detection, cf. FIG. 7D). In some embodiments, a bidirectional test cartridge has the sample port located between two test areas on the top side of that test cartridge. Accordingly, the sample port of this test cartridge passes through the entrance of the enclosure, as all other sample port areas remain on the proximal side of the entrance of the enclosure and maintain a nominal inserted height. Accordingly, the bidirectional test cartridge requires that the enclosure entrance is higher, to allow the sample port to pass through. Accordingly, the light shield may be mechanically activated when a test cartridge is fully inserted by means of a simple cam lever, thus preventing any ambient light interference through the heightened enclosure entrance. The enclosure entrance is then lowered in contact with the top surface of the test cartridges, blocking off the additional height of the cartridge mount entrance, and in the process also blocking ambient light leakage inside the dark chamber.

FIG. 8B illustrates a cartridge mount that includes a small flexure that depresses the presence switch when a cassette is inserted, according to some embodiments. This configuration avoids a pushback of the test cartridge when the switch acts along the entry direction. Additionally, there is a light shield that has flexures that are pushed down to block light when the test cartridge is inserted. The presence switch is cycled once with every test cartridge insertion (e.g., once for every test). In some embodiments, a safety factor of 10×, and the switch may be selected to cycle about 7,200 times, or less, for a desired lifetime of the image-capturing device. This is well within the ratings of available commercial switches (e.g., TE Connectivity part #: JJEVOUG380NOHPMRTR) is rated for 100,000 cycles; see Table 3 below).

TABLE 3

Exemplary Switch Lifetime Specifications (JJE-NOH)

| Contact Rating | 10 mA, 5 VDC Max |
|---|---|
| Contact Resistance | 1Ω Max. |
| Insulation Resistance | 100 MΩ Min. |
| Dielectric Strength | 100 VAC/1 minute |
| Operating Force | 36 gF Max. |
| Travel | 2.5 mm |
| Operating Life | 100,000 cycles |
| Operating Temperature | −40° C. to 85° C. |
| Storage Temperature | −40° C. to 85° C. |

Figure 9:
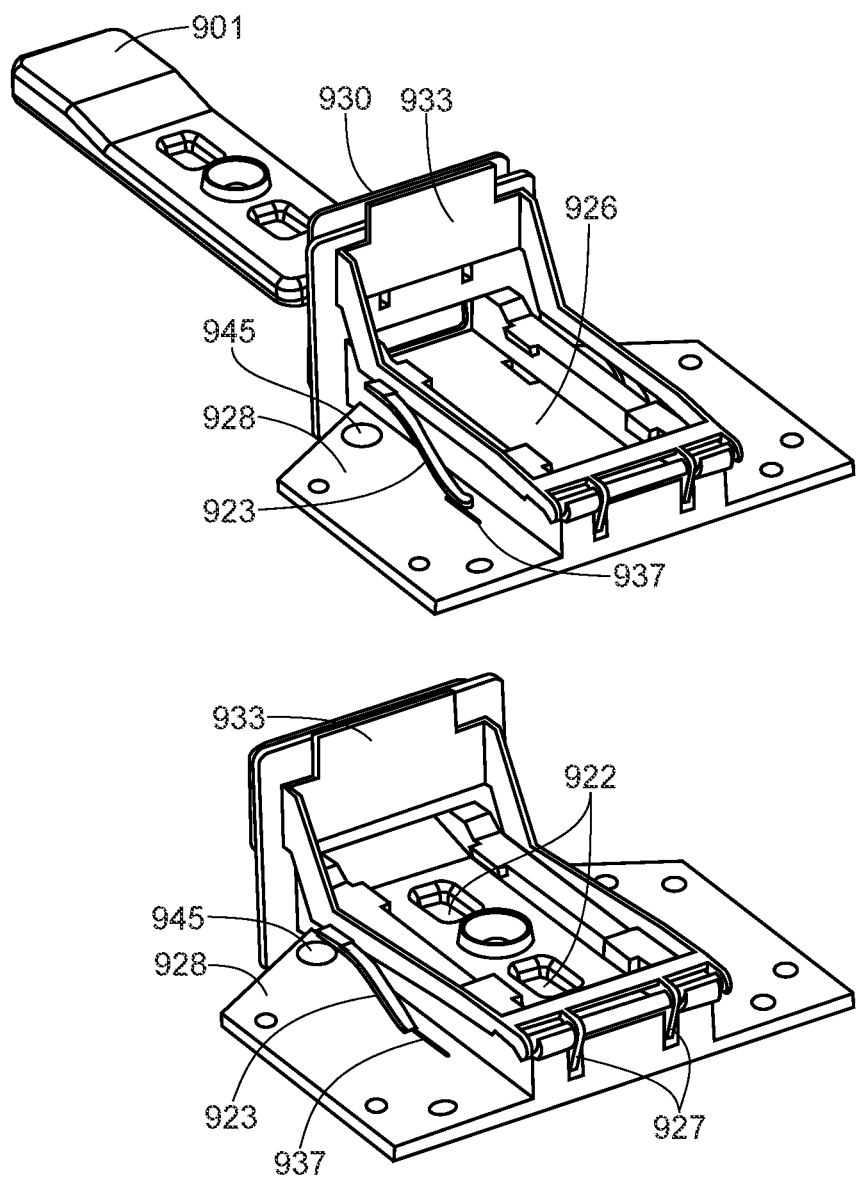
FIG. 9 is a perspective view of a cartridge mount including a light shield, leaf springs, and door actuation levers for receiving a test cartridge in the enclosure of an image-capturing device, according to some embodiments.

FIG. 9 is a perspective view of a cartridge mount 926 including a light shield 930, leaf springs 923, and door actuation levers 927 for receiving a test cartridge 901 in the enclosure of an image-capturing device (e.g., image-capturing devices 100A, 200, 300, 400, 500, 600, and 700), according to some embodiments. In some embodiments, a base member 928 is configured to receive a test cartridge 901 having reading zones 922. A light shield 930 is positioned on base member 928. Light shield 930 includes a cam lever 933 that engages with test cartridge 901 to cause light shield 930 to move from a first position (e.g., 'open') to a second position (e.g., 'closed').

In some embodiments, base member 928 includes a sensor 945 to identify and communicate receipt of a test cartridge. In some embodiments, sensor 945 may include a contact sensor, such as a capacitive sensitive contact element, or an electric switch. In some embodiments, sensor 945 may include an optical sensor, an inductive sensor, a magnetic sensor, and the like. Light shield 930 may include a pair of leaf springs 923 to hold light shield 930 in a first position. In some embodiments, base member 928 includes a groove 937 to receive a u-shaped portion of each leaf spring 945 when light shield 930 is in its second position (e.g., closed).

Figure 10:
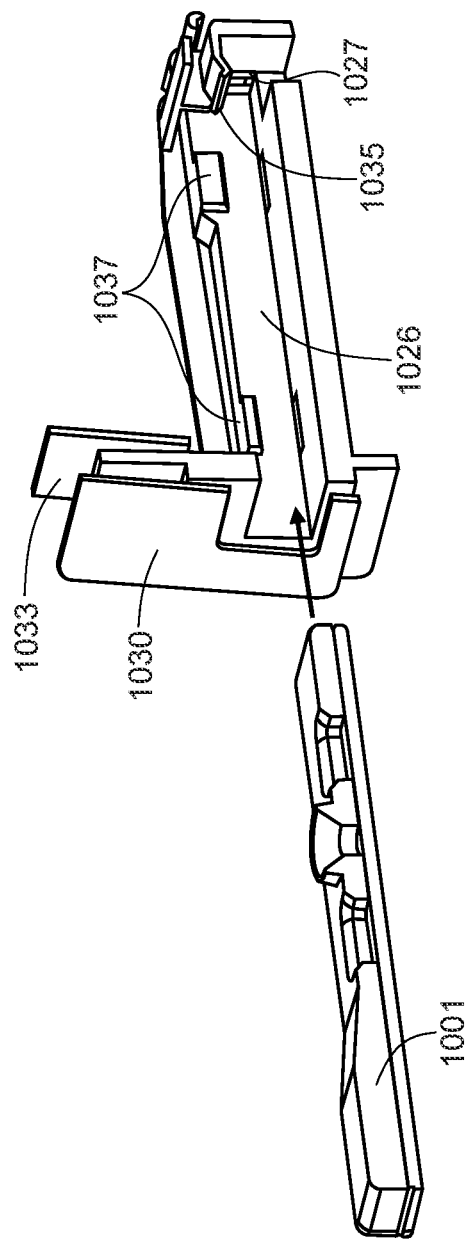
FIG. 10 is a close-up perspective view of a test cartridge inserted in a cartridge mount of an image-capturing device, according to some embodiments.

FIG. 10 is a close-up perspective view of a test cartridge 1001 inserted in a cartridge mount 1026 of an image-capturing device, according to some embodiments. Cartridge mount 1026 includes a light shield 1030 configured to snap in place upon action of cam lever 1033. Shield 1030 blocks any ambient light from illuminating test cartridge 1001 when it is in place against a door actuation lever 1027. In some embodiments, a retainer flexure 1035 presses onto test cartridge 1001 to fix it in cartridge mount 1026. Cartridge guides 1037 enable positioning of test cartridge 1001 in cartridge mount 1026.

Figure 11A:
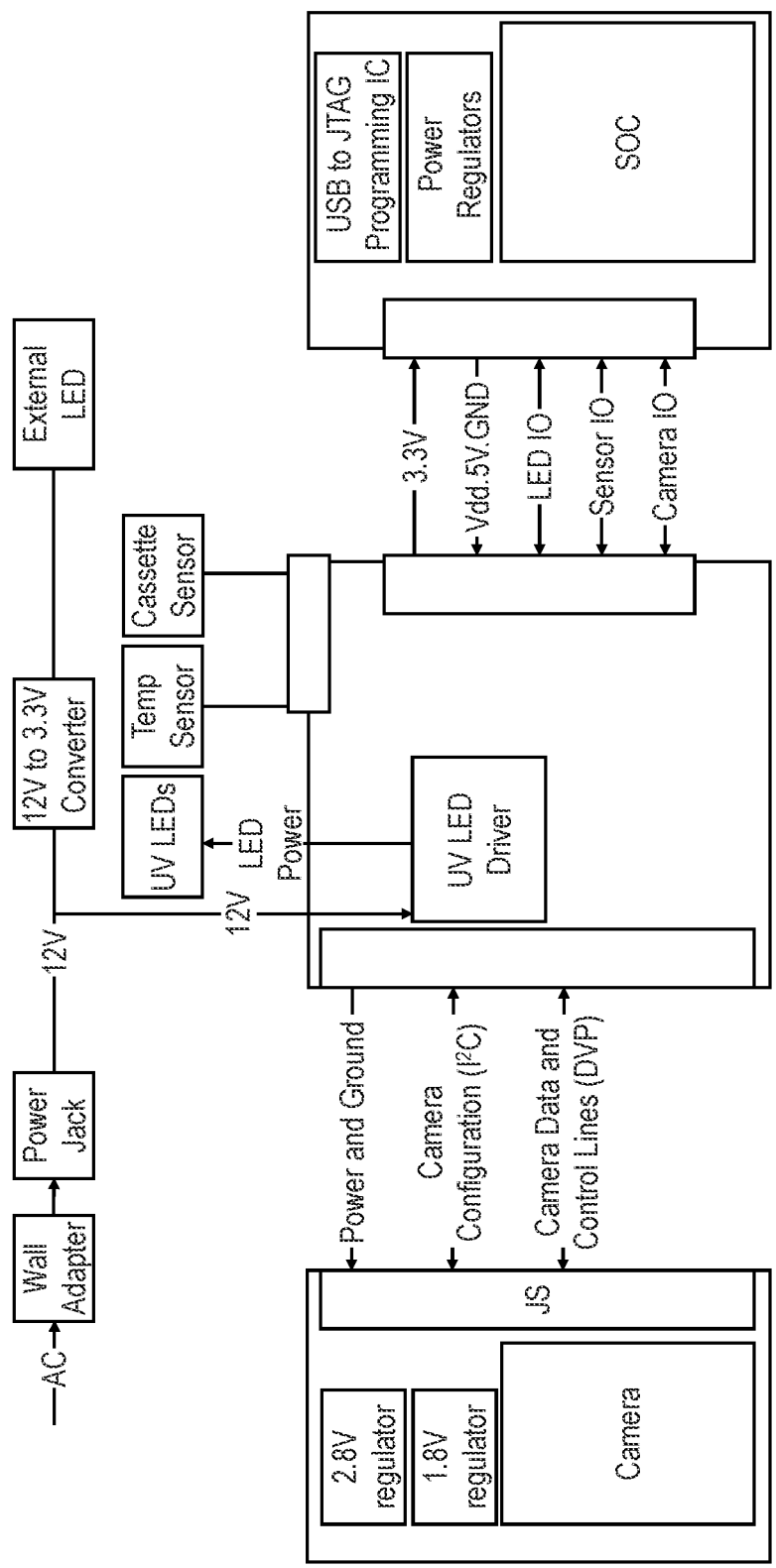
FIGS. 11A-11C illustrate system block diagrams of the electronic components in an image-capturing device, according to some embodiments.
Figure 11B:
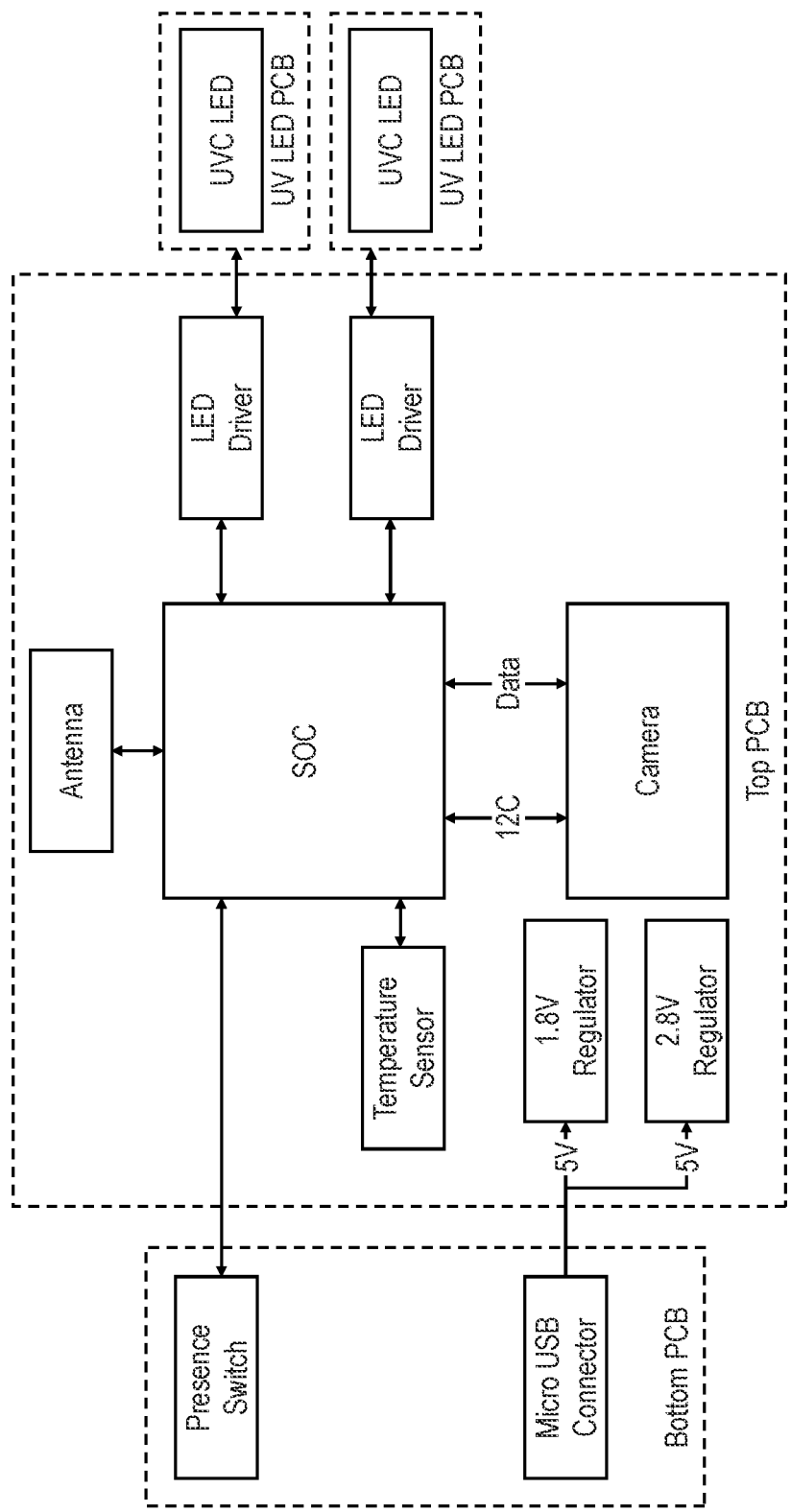
Figure 11C:
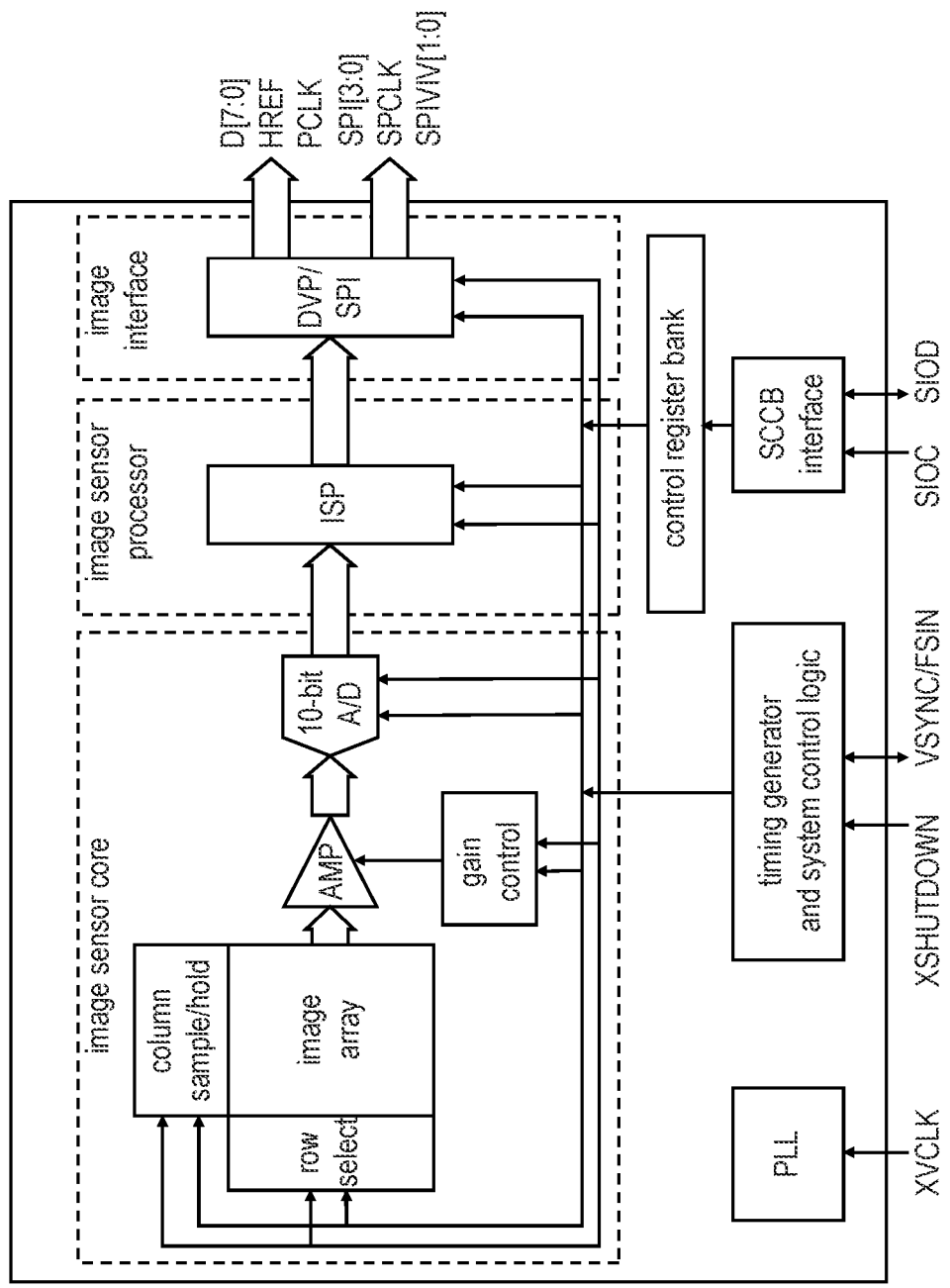

FIGS. 11A-11C illustrate system block diagrams of the electronic components in an image-capturing device, according to some embodiments. The user interacts with the image-capturing device via an application installed, e.g., in a client device (cf. application 122 in client device 110 or smart phone, and the like). Some of the relevant electronic components include a sensor array and driver, one or more light sources and a light source driver, and the SoC, in addition to other power regulators, converters, adaptors, and interconnects. Some embodiments include a temperature sensor and a test cartridge presence detector, as discussed earlier.

In one embodiment, the image-capturing device is identified through a unique alphanumeric identifier or identification (ID) corresponding to, for example, the last four characters of the BLE media access control (MAC) address of the SoC. The image-capturing device becomes functional and discoverable (e.g., by the smart phone or other client device running the application) upon connection of the USB-C compliant connector. This allows pairing of the image-capturing device with the smart phone or client device through Bluetooth radio. Once the image-capturing device and the client device are paired, the application can trigger and schedule a series of functions in the image-capturing device that include turning light source ON/OFF, adjusting sensor array performance characteristics (e.g., exposure, transfer of images through the BLE), temperature reading, and testing metadata.

Upon full insertion of a test cartridge, a light shield mechanism is actuated to enclose the distal end of the test cartridge and blocks stray light from entering the optics chamber (cf. FIGS. 4A-4F). The test cartridge presence sensor is also triggered, which indicates the start of the immunodiagnostic test timer for image capture.

When triggered, an image of one or more test window(s) in the test cartridge is captured in the absence of illumination and transferred as a dark image. After this transfer is complete, the test window will be illuminated homogeneously using the two UV LEDs and the illuminated image transferred (light image). The dark image will be used to ensure no stray light is entering the optical chamber. The light image will be used for running a quality control (QC) algorithm to ensure that the test runs properly, on a calibrated test cartridge, without non-specific binding. In some embodiments, the images may be cropped before transfer to minimize file size and speed of transfer, while capturing critical information for the assay. In some embodiments, some data analysis may be performed in the image-capturing device. In yet other embodiments, the image-capturing device performs no substantive data analysis prior to transmitting the image to the paired client device.

In some embodiments, the data analysis of the two images (dark/light) per test is performed by the application running in the client device. The dark image is analyzed for the presence of stray light, while the light image is analyzed consecutively through a QC algorithm to ensure the image meets specific QC criteria. In some embodiments, an adjudication algorithm (e.g., machine learning, artificial intelligence, and the like) may be used to determine the status of the assay for each analyte.

FIG. 11C illustrates a functional block diagram of a sensor array driver, according to some embodiments. In some embodiments, the sensor array includes a colored CMOS sensor (e.g., OmniVision OV7676, 1/7.5-inch VGA CMOS). Some relevant features to select a sensor array may include: the quality of the images generated, the limit of detection (sensitivity) for analytes on typical Immunodiagnostic assays on standard commercial test cartridges, pricing in scale of production and the manufacturer's commitment to maintain the line of product.

The image sensor core generates streaming pixel data at a constant frame rate. The sensor driver samples each pixel analog value, converts it to a 10-bit digital value, and then streams it over a digital interface to the image sensor processor. Some configurations (e.g., for tests, or quick runs, checkups, and the like) may use an 8-bit digital conversion. Accordingly, the range for pixel intensity is from 0 to $2^{10}$ (or $2^8$, in some configurations).

In some embodiments, the sensor array includes an image interface that supports multiple digital streaming formats. Additionally, the image interface may include a two-wire interface ($I^2C$). In some embodiments, the image interface uses a Digital Video Port (DVP) interface. In some embodiments, the image interface may use a serial port interface (SPI), e.g., a single channel-SPI, or a parallel (4-bit) SPI interface. The specific choice of image interface may depend on device compatibility, speed, accuracy, and other considerations.

FIG. 12 illustrates a block diagram of an interface between an SoC and a sensor array in an image-capturing device, according to some embodiments. In some embodiments, the SoC may include a microprocessor and a radio device (e.g., Bluetooth Radio) configured to drive an RF antenna. Accordingly, in addition to cost considerations, it is desirable that the SoC of choice (e.g., Nordic nRF52840 SoC) have a built-in BLE 5.0 capability, which offers both the highest distance and speed for data transfer to a Bluetooth device. BLE 5.0 protocols also offer a superior level of security, as well as a programmable input/output (10) that allow direct interface with the sensor array.

Some tradeoffs to consider may include RAM and computational power to process the images from the sensor array. The primary external interfaces to the SoC may include: Camera data interface; Camera configuration interface; Sensors—temperature and test cartridge presence; UV LED Drivers (x1, x2, and the like); Status LEDs (x1, x2, and the like); RF Antenna Interface; Processor specific peripherals (input clock, programming pins, and debug port).

The digital IO lines in the SoC can be configured for various functions, as follows: The transfer of an image is framed by the toggling of the VSYNC line, each toggling representing a new frame; Horizontal Refresh (HREF) line marks the presence of valid row data; Pixels are sent in groups of 640, i.e., one row at a time within each HREF pulse; The image data is sent via 8 GPIO data lines sending one pixel's worth of data in parallel per cycle of the pixel clock (PCLK) for every pixel in a given frame. In some embodiments, the pixel clock is configured for 2.5 MHz and data is captured at that rate. In some embodiments, for frames to be provided, the rate of capture and transmission of the images through the SoC must be controlled appropriately.

In some embodiments, a sensor array may use an $I^2C$ protocol for configuring settings, such as exposure. Accordingly, one wire for the $I^2C$ clock and one wire for $I^2C$ data couples the SoC and the sensor array. A Two-Wire Interface (TWI) peripheral of the SoC implements the $I^2C$ protocol and is used to configure the sensor array. A clock (SCL) and data lines (SDA) are coupled as shown.

Figure 13A:
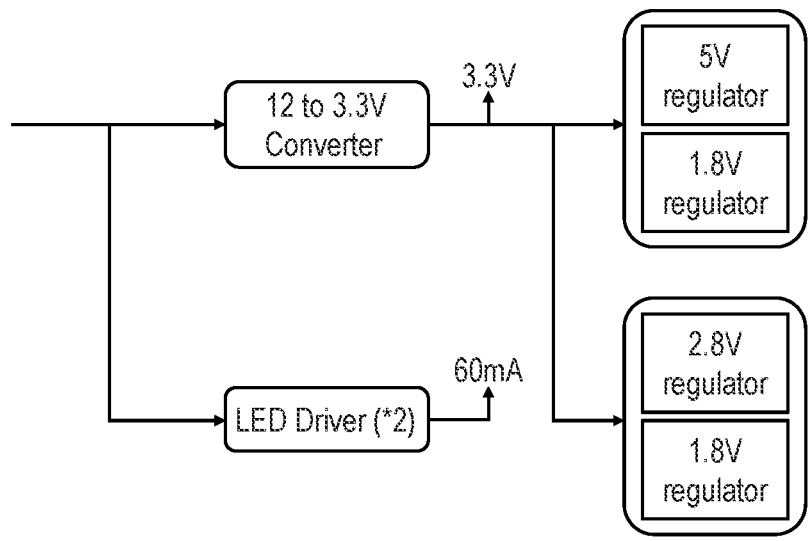
FIGS. 13A-13B illustrate block diagrams of a power distribution unit in an image-capturing device, according to some embodiments.
Figure 13B:
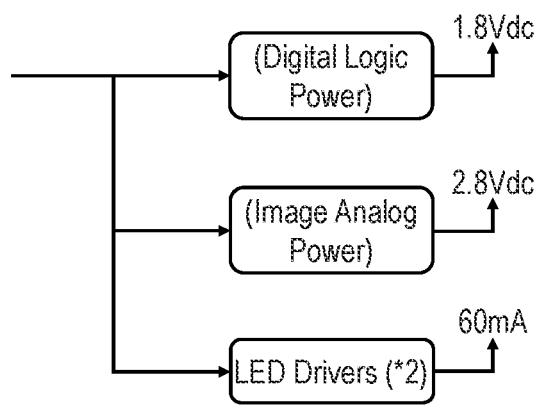

FIGS. 13A-13B illustrate block diagrams of a power distribution unit in an image-capturing device, according to some embodiments. In some embodiments, a power distribution unit is designed so that it can be powered via any standard commercially available USB power adapter.

FIG. 13A illustrates one embodiment configured to receive a 12 V supply to satisfy the power requirements of a commercially available development board. The SoC board and sensor array board each have their own internal power supplies to generate the voltages required, as shown.

FIG. 13B illustrates a power distribution unit without redundant supplies, allowing for operation with a 5V input from a USB port. Additionally, the system may be optimized for low power to maintain a maximum power consumption below the recommended USB power limits. The system ensures maximum power less than 2.5 W (5V at 500 mA), with a target of half that, to ensure margin. In some embodiments, newer generation of USB adapters providing higher power may be used, if desired. In the specific power distribution unit illustrated, the 5V input is used to generate a 1.8 Vdc for the digital logic for the processor and image sensor, a 2.8 Vdc for the sensor array (analog voltage), and a constant 60 mA for the UV LEDs when illumination is enabled.

The maximum calculated power consumption of the illustrated unit is less than about 1.1 W. An exemplary power budget of the system illustrated in FIGS. 11A-11C is shown below in Table 4. Typical consumption is in the idle state—when the image-capturing device is waiting for image capture and providing status over BLE. The maximum current case is during a light image capture when the light sources are enabled and the image is being captured.

TABLE 4

Exemplary Power Budget

|  |  |  | 5V (from USB) | | | |
| --- | --- | --- | --- | --- | --- | --- |
| Device | PN | QTY | Typ | Max | Total (typ) | Total (max) |
| Nordic SoC (1.8 V Power) | nRF52840-QIAA | 1 | 16.00 | 32.00 | 16.00 | 32.00 |
| Camera 1.8 V | TLV70018DDCT | 1 | 17.00 | 24.00 | 17.00 | 24.00 |
| Camera 2.8 V | TLV70028DDCT | 1 | 15.00 | 20.00 | 15.00 | 20.00 |
| UV LED Drivers | AL5802 | 2 | 0.00 | 60.00 | 0.00 | 120.00 |
| Status LED | QBLLP653 | 1 | 10.00 | 10.00 | 10.00 | 10.00 |
| Temperature Sensor | LMT01 | 1 | 0.08 | 0.14 | 0.08 | 0.14 |
| Cassette Sensor |  | 1 | 0.00 | 0.10 | 0.00 | 0.10 |
| Total |  |  |  |  | 58.1 | 206.1 |
| Power (mw) |  |  |  |  | 290.4 | 1030.7 |

Figure 14:
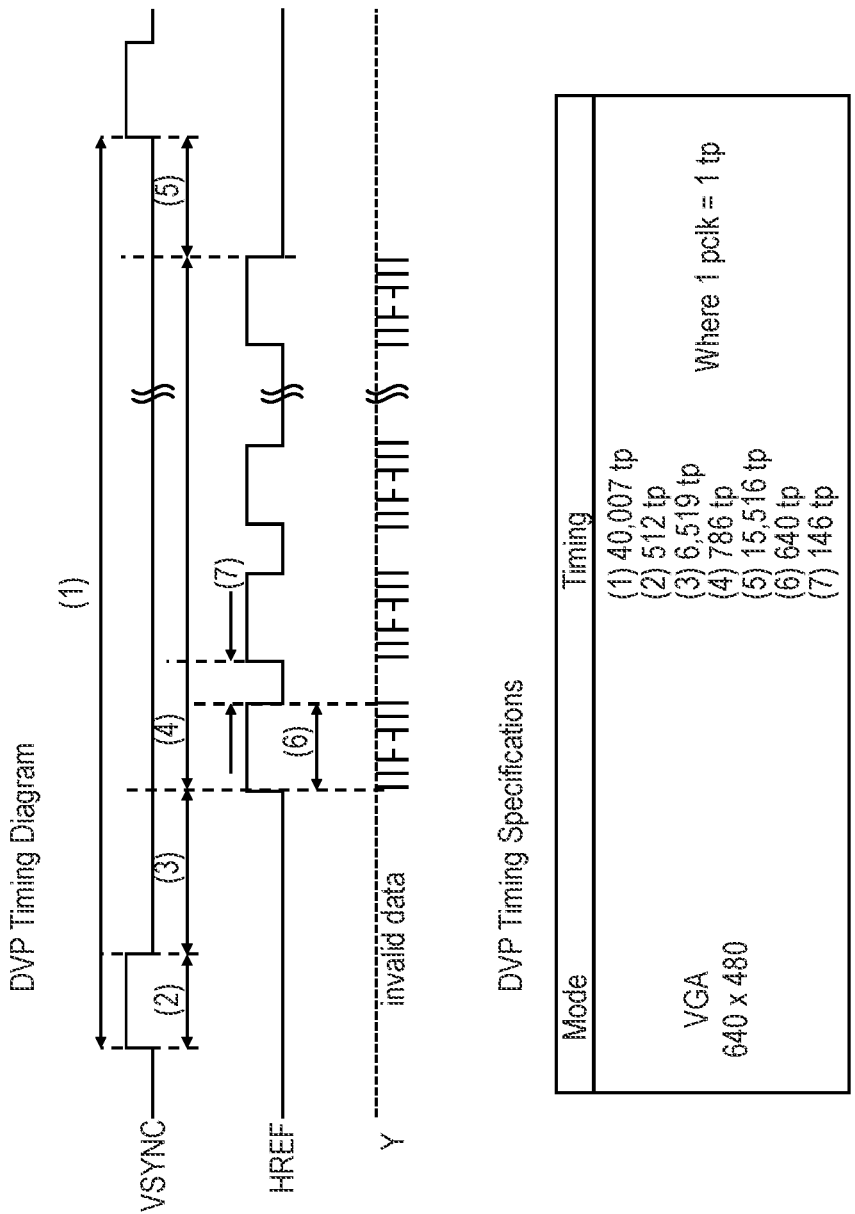
FIG. 14 illustrates a timing diagram including signal and power waveforms in an image-capturing device, according to some embodiments.

FIG. 14 illustrates a timing diagram including signal and power waveforms in an image-capturing device, according to some embodiments. The image interface of the sensor array (e.g., DVP interface, cf. FIG. 11C) has a defined set of control lines, data lines, and timing to capture the image data. The timing diagram provides the timing of VSYNC, HREF, and data relative to a pixel clock period (cf. Exemplary IO Pin Configuration, above).

Figure 15:
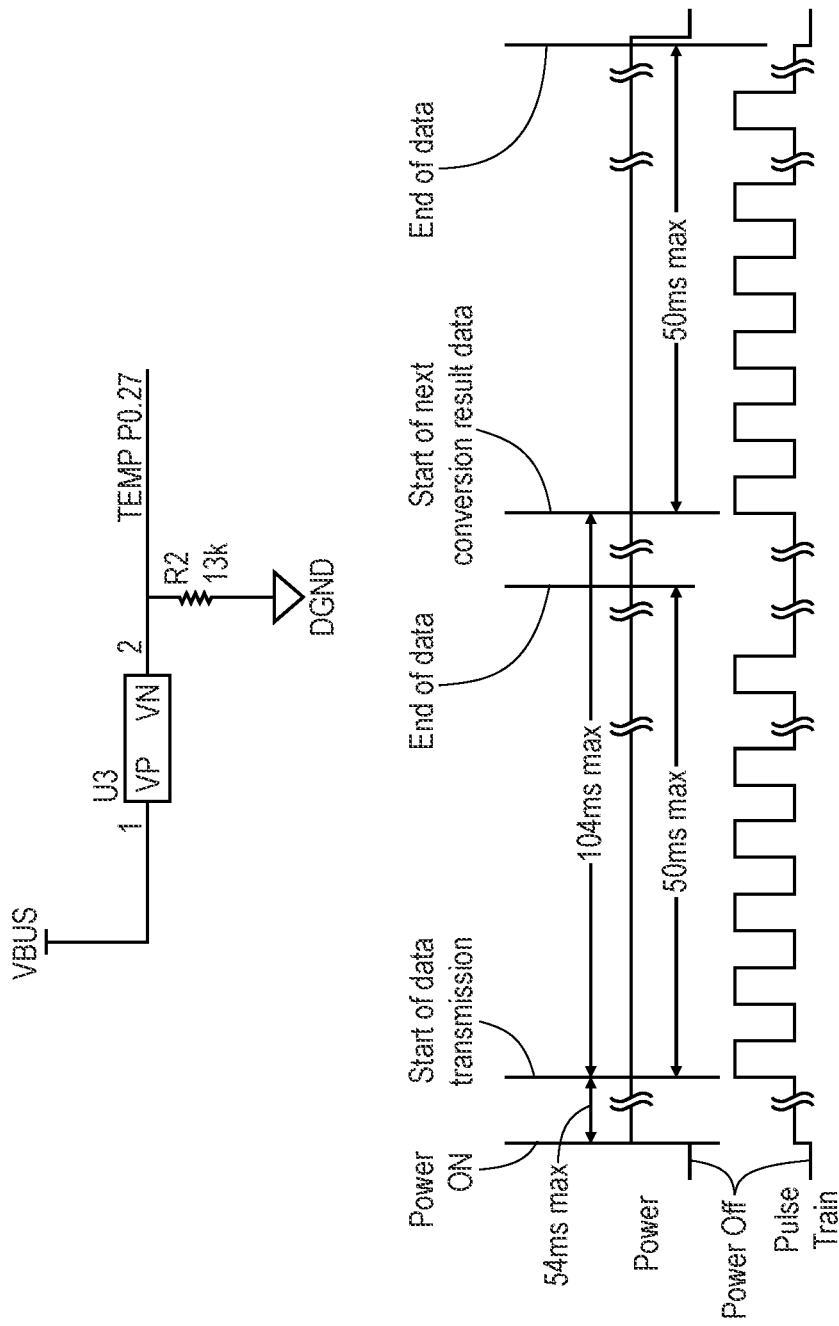
FIG. 15 illustrates a temperature sensor schematic and a key waveform for driving the temperature sensor, according to some embodiments.

FIG. 15 illustrates a temperature sensor schematic and a key waveform for driving the temperature sensor, according to some embodiments. In some embodiments, the temperature sensor is a one-wire digital interface to the SoC. The temperature sensor may be powered via the 5V input and outputs a pulse train every 104 milliseconds (maximum, cf. FIGS. 13A-13B, and 14). The processor counts the pulses to determine temperature. The resistor on the output of the sensor (R2) sets the output voltage levels. A resistor of about 13 kohm sets the output level at voltages compatible with the SoC logic voltage (e.g., Logic high=13 kohm×125 µA=1.625V, logic low=13kohm×34 µA=0.44V).

Figure 16:
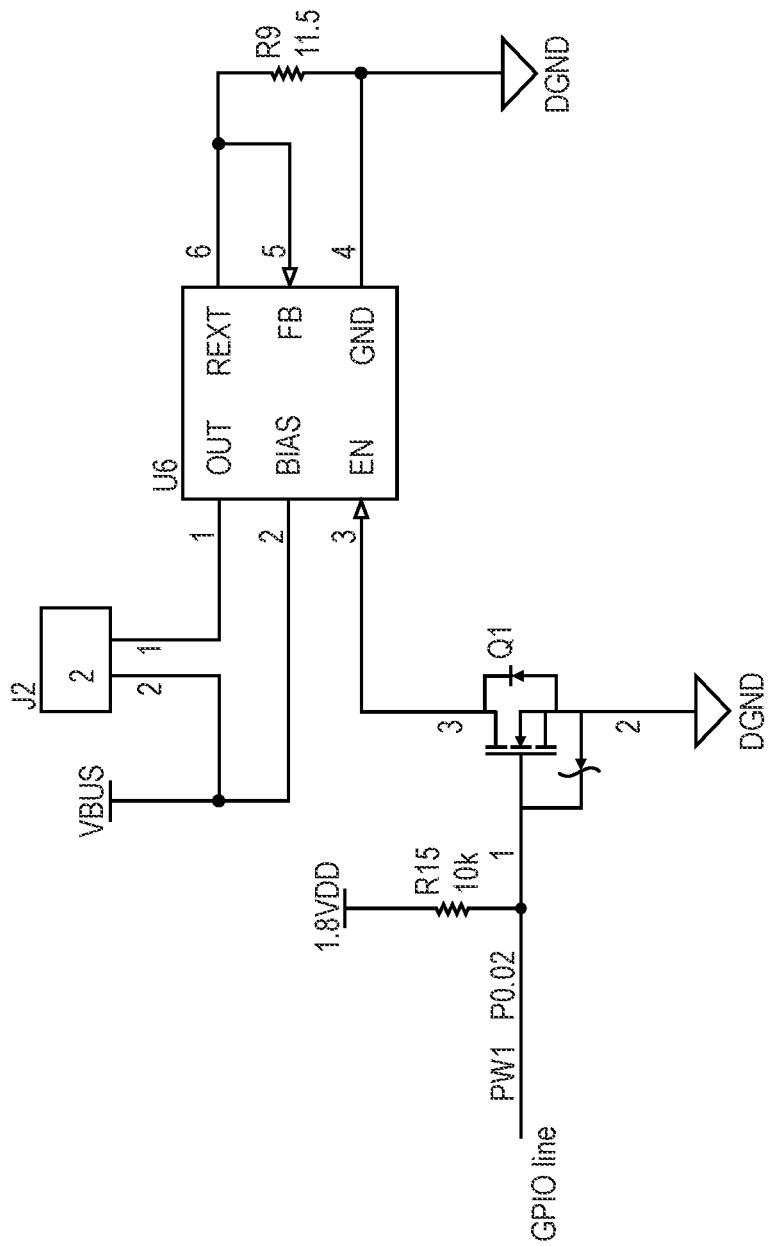
FIG. 16 illustrates a driver circuit for a light source in an image-capturing device, according to some embodiments.

FIG. 16 illustrates a driver circuit for a light source in an image-capturing device, according to some embodiments (cf. FIGS. 11A and 11B). In some embodiments, the light source driver is enabled via a control line to the SoC. In some embodiments, the light sources may be controlled at a constant 60 mA current via the driver ICs when enabled by the SoC. The light source current is set through R9 as in: current=0.7V (internal reference)/R9 (external resistor, e.g., 11.5 ohm).

Figure 17A:
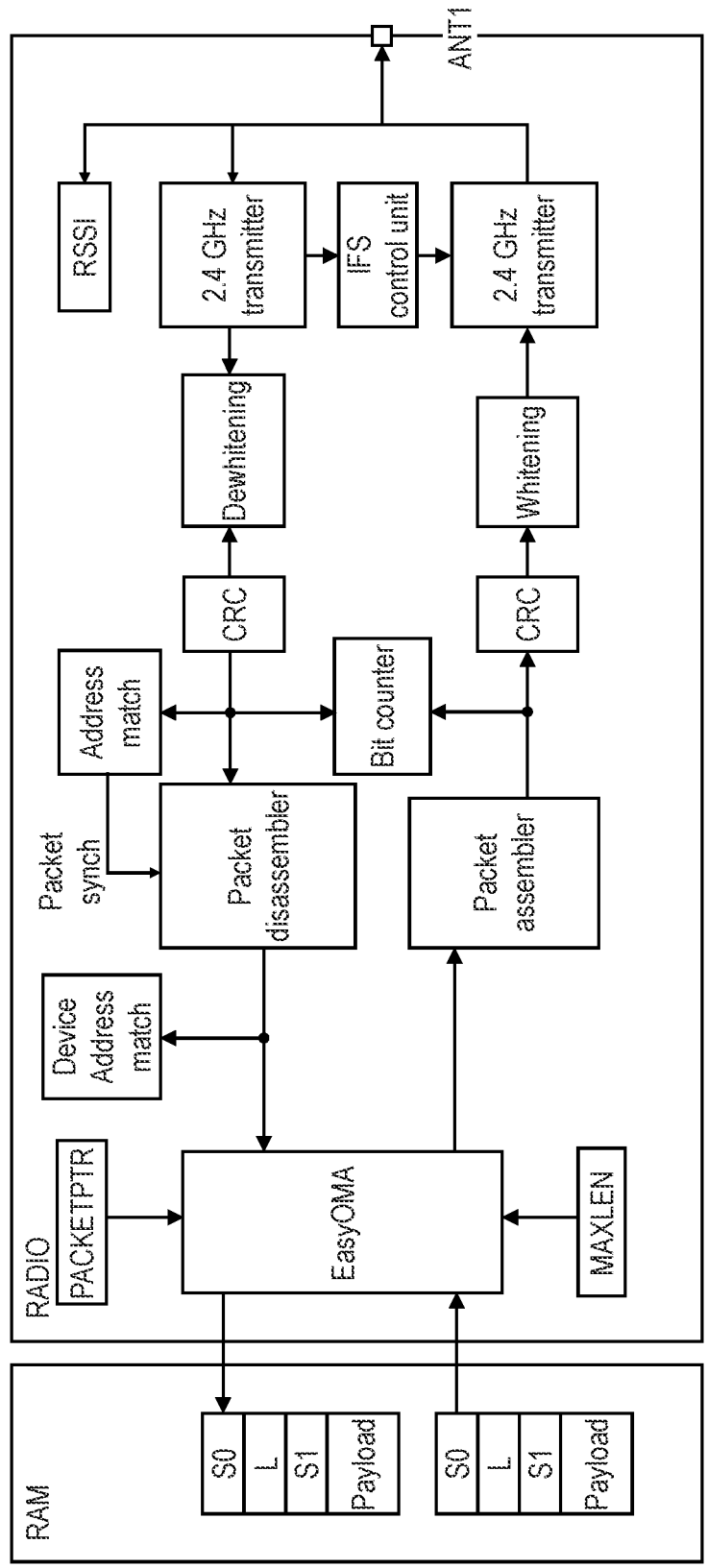
FIGS. 17A-17B illustrate an antenna interface and a radio block diagram in an image-capturing device, according to some embodiments.
Figure 17B:
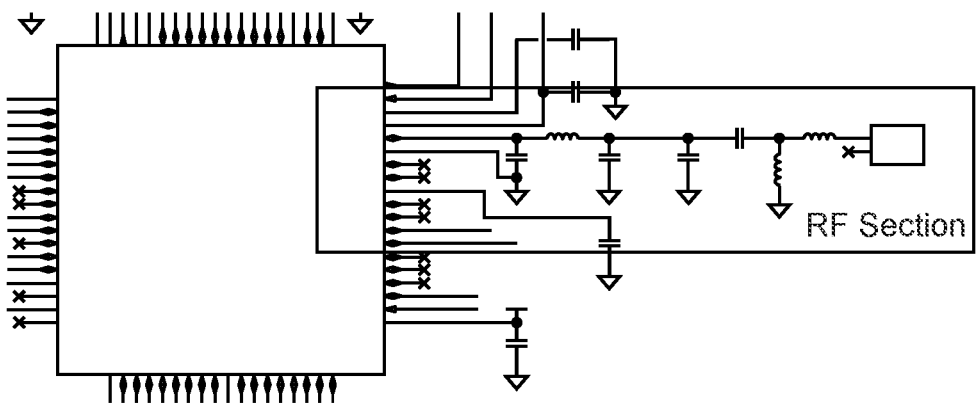

FIGS. 17A-17B illustrate an antenna interface and a radio block diagram in an image-capturing device, according to some embodiments.

FIG. 17A illustrates a radio-antenna interface, according to some embodiments. In some embodiments, the SoC includes a built-in 2.4 GHz transceiver that is compatible with multiple radio standards (e.g., BLE 5.0). This radio block handles all the conversion to/from the RF antenna and presents the data through a standard internal memory interface. In some embodiments, the radio circuitry may be included in the SoC, and the RF antenna may be external to the SoC.

FIG. 17B illustrates a schematic diagram of the RF components coupling an external antenna to the BLE radio terminals in the SoC, according to some embodiments. The RF inductor values and capacitors are adjusted accordingly to obtain a desired fidelity, accuracy, and compatibility with the specifications of the SoC circuit of choice.

Figure 18:
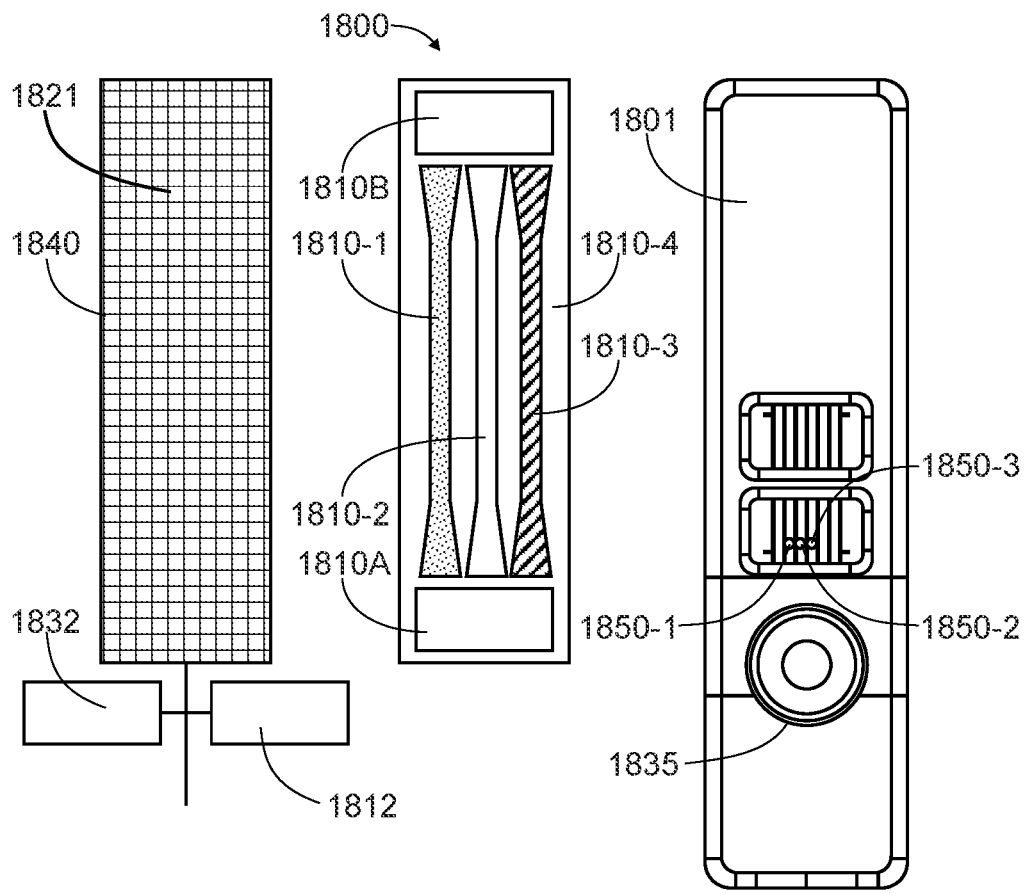
FIG. 18 illustrates a mask having multiple portions used to filter the light received by a sensor array in an image-capturing device, according to some embodiments.

FIG. 18 illustrates a mask 1800 having multiple portions 1810A, 1810B, 1810-1, 1810-2, 1810-3, and 1810-4 (hereinafter, collectively referred to as "mask portions 1810"), used to filter the light received by a sensor array 1840 in an image-capturing device, according to some embodiments. Sensor array 1840 includes a plurality of light sensitive pixels 1821. In some embodiments, an image-capturing device may further include mask 1800 placed between a lens mount (e.g., lens mounts 407-1 or 607-1) and sensor array 1840. In some embodiments, filter mask 1800 allows a selected wavelength of light to access each of a selected one of the plurality of pixels 1821. In some embodiments, sensor array 1840 may include a complementary metal-oxide-semiconductor (CMOS) circuit. Further, in some embodiments, sensor array 1840 may include single color pixels, or multi-color pixels, e.g., Red, Green, and Blue, RGB, pixels.

In some embodiments, mask 1800 is disposed adjacent sensor array 1840 and includes one or more dielectric material layers to transmit light of a desired wavelength to light sensitive pixels 1821 in sensor array 1840. Each mask portion 1810 is adjacent to one or more light sensitive pixels 1821. And each mask portion 1810 transmits light in a pre-selected wavelength region of an electromagnetic spectral range. In some embodiments, mask 1800 is disposed over sensor array 1840 such that a portion of the image of a sensitive area in a test cartridge 1801 overlaps with at least one of mask portions 1810.

Accordingly, a pre-selected wavelength region of the electromagnetic spectral range transmitted by mask portion 1810 is selected based on a portion of the image of the sensitive area in test cartridge 1801. In some embodiments, the portion of the image of the sensitive area in test cartridge 1801 includes a reagent sensitive to one of multiple analytes of interest in a test sample provided through a sample port 1835, and the pre-selected wavelength region includes at least a portion of an emission spectrum of an emitter associated with the reagent. For example, the portion of the image of the sensitive area in test cartridge 1801 may be a detection channel 1850-1, 1850-2, or 1850-3 (hereinafter, collectively referred to as "detection channels 1850") for a specific analyte A, having a fluorescent tag or bead emitting light with a selected wavelength, $\lambda_i$. Detection channels 1850 may include flow paths in a lateral flow immunoassay. Accordingly, a mask portion 1810 overlapping the detection channel for analyte A may include dielectric layers configured to transmit light at wavelength $\lambda_i$ to underlying light sensitive pixels 1821. In some embodiments, one or more of detection channels 1850 may be associated with a test line and one or more of detection channels 1850 may be associated with a control line (e.g., test lines 506t and control lines 506c).

In some embodiments, at least one of mask portions 1810 blocks a light in a selected wavelength region of the electromagnetic wavelength range from reaching light sensitive pixel 1821. In some embodiments, mask portions 1810 are selected to allow sensor array 1840 to independently detect signals from any one of multiple analytes of interest in test cartridge 1801.

In some embodiments, sensor array 1840 is coupled to a memory circuit 1832 and to a processor circuit 1812. Accordingly, memory circuit 1832 may store instructions which, when executed by processor circuit 1812, cause sensor array 1840 to select a first group of pixels 1821 to form a first signal and a second group of pixels 1821 to form a second signal. For example, the first group of pixels may overlap a first mask portion 1810-1, and the second group of pixels may overlap a second mask portion 1810-2. Accordingly, the first signal may be associated with light of a first wavelength range from a first analyte of interest in the sample and the second signal is associated with light of a second wavelength range from a second analyte of interest in the sample.

In some embodiments, the spectral transmissivity of each mask portion 1810 is selected according to increase selectivity and discrimination between different fluorescence emission bands of at least two or more reagents used in a lateral flow immunoassay.

Figure 19:
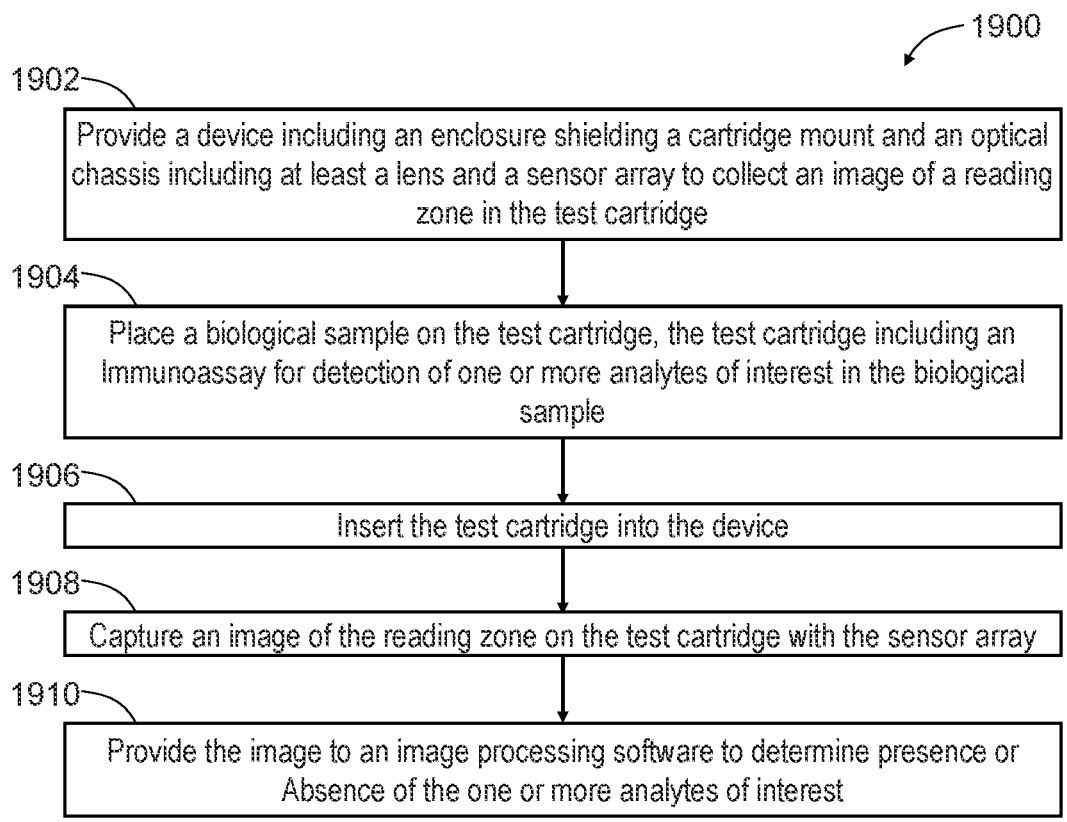
FIG. 19 is a flow chart illustrating steps in a method for determining the presence or absence of an analyte of interest, according to some embodiments.

FIG. 19 is a flow chart illustrating steps in a method 1900 for determining the presence or absence of an analyte of interest, according to some embodiments. Methods consistent with the present disclosure may include at least one or more of the steps in method 1900 performed at least partially by one or more devices in an architecture including a remote server, a database, a client device, and an image-capturing device as disclosed herein (e.g., architecture 10, remote server 130, database 152, client device 110, and image-capturing devices 100). Either one of the server, the database, the client device, and the image-capturing device may include a memory circuit storing instructions and a processor circuit configured to execute the instructions to perform, at least partially, one or more of the steps in method 1900 (e.g., memory circuits 132, 432, 532, 632, 732, and 1832, and processor circuits 112, 412, 512, 612, 712, and 1812). In some embodiments, at least one or all of the server, the database, the client device, or the image-capturing device may include a communications module configured to transmit and receive data to one or more of the devices in the architecture, through a network or via a one-to-one (wired or wireless) communication channel (e.g., communications modules 118 and network 150). The image-capturing device may include an enclosure enshrouding an optical assembly and a cartridge mount (e.g., enclosure 120, 220, and 420, optical chassis 224, 324, 424, 624, and 724, and cartridge mounts 226, 336, 426, 526, 726, 926, and 1026). The cartridge mount may be configured to receive a test cartridge, and the optical assembly may include a lens mount and at least one light source mount movable with respect to each other (e.g., test cartridges 101, 501, 601, 801, 901, and 1001, and optical mounts 407 and 607). The light source mount may support a light source configured to illuminate the test cartridge (e.g., light sources 437, 637, and 737). The lens mount may support a lens configured to project an image of the illuminated test cartridge onto a sensor array disposed in the optical assembly. The image of the illuminated test cartridge may include at least a portion of a reading zone in the test cartridge, delimited by a border line.

In some embodiments, methods consistent with the present disclosure may include at least one step from method 1900, or more than one step from method 1900 performed in a different order or overlapping in time. For example, some embodiments consistent with the present disclosure may include one or more steps in method 1900 performed simultaneously, or quasi-simultaneously.

Step 1902 includes providing the image-capturing device, including an enclosure shielding a cartridge mount and an optical chassis including at least a lens and a sensor array to collect an image of a reading zone in the test cartridge.

In some embodiments, step 1902 includes calibrating the image-capturing device. In some embodiments, step 1902 may include adjusting the camera focusing. In some embodiments, step 1902 may include calibrating the temperature sensor.

Step 1904 includes placing a biological sample on a test cartridge including an immunoassay for detection of one or more analytes of interest in a sample. In some embodiments, the sample is a biological sample, such as a body fluid (e.g., blood, serum, plasma, sputum, mucus, saliva, tear, or urine). In some embodiments, the body fluid may be of human origin. In some embodiments, the immunoassay includes reagents for detection of an infectious agent (e.g., a virus or a bacterium). In some embodiments, the immunoassay includes reagents for detection of one or more protein biomarkers, or an autoantibody. In some embodiments, the immunoassay is configured for detection of two (2) to twenty (20), or more, analytes of interest. In some embodiments, step 1904 includes flowing the biological sample on multiple test channels for detection of 2-20 analytes of interest.

Step 1906 includes inserting the test cartridge into the device.

Step 1908 includes capturing an image of a reading zone on the test cartridge with the sensor array.

Step 1910 includes providing the image to an image processing circuit to determine presence or absence of the one or more analytes of interest. In some embodiments, step 1910 further includes detecting an emission of a unique signal associated with each analyte in the analytes of interest in the sample.

The immunoassay test strip mentioned above, such as that in test cartridge 101, may be configured uniquely for detection of a particular pathogen or analyte of species of interest. These include, but are not limited to, proteins, haptens, immunoglobulins, enzymes, hormones, polynucleotides, steroids, lipoproteins, drugs, bacterial antigens, and viral antigens. With regard to bacterial and viral antigens, more generally referred to in the art as infectious antigens, analytes of interest include Streptococcus, Influenza A, Influenza B, respiratory syncytial virus (RSV), hepatitis A, B, and/or C, pneumococcal, human metapneumovirus, Corona viruses (e.g., SARS-Cov2), and other infectious agents well-known to those in the art. Test assays that detect one or more analytes of interest are contemplated. In some embodiments, a test device is intended for detection of one or more of antigens associated with Lyme disease. In some embodiments, an immunoassay test strip is intended for use in the field of women's health. In other embodiments, test devices for detection of one or more of fetal-fibronectin, chlamydia, human chorionic gonadotropin (hCG), hyperglycosylated chorionic gonadotropin, human papillomavirus (HPV), and the like, are contemplated. In another embodiment, an immunoassay test strip for detection of vitamin D contemplated. Test strips for detection of diseases or cardiac conditions are also contemplated.

An exemplary immunoassay test strip may include a sample-receiving zone in fluid communication with a label zone. A fluid sample placed on or in the sample zone flows by capillary action from the sample zone in a downstream direction. A label zone is in fluid communication with at least a test line or band and, optionally, a control line or band and/or a reference line or band. Typically, the label zone is downstream from the sample zone, and the series of control and test lines are downstream from the label zone, and an optional absorbent pad is downstream from the portion of the test strip on which the lines are positioned.

The sample zone receives the sample suspected of containing an analyte of interest. The label zone, in some embodiments, contains two dried conjugates that are comprised of particles containing a label element. The label element includes a label that emits a signal in any of a number of selected emission processes: e.g., electromagnetic radiation, alpha particle radiation, positron radiation, beta radiation, and the like. In some embodiments, the electromagnetic radiation emission may include a fluorescence emission, Raman emission, and the like. Further, in some embodiments, the label may absorb a selected type of radiation, e.g., electromagnetic radiation as in microwave absorption, infrared (IR) absorption, visible absorption, or ultraviolet (UV) absorption. Further, in some embodiments, the label element may include multiple label elements selected from all or more of the above radiation emission and/or absorption described above.

Without loss of generality, and to illustrate the operation of the system at hand, in one embodiment, the label element may include a fluorescent compound of an element. An exemplary fluorescent element is a lanthanide material, such as one of the sixteen elements lanthanum, cerium, praseodymium, neodymium, promethium, samarium, europium, gadolinium, thulium, terbium, dysprosium, holmium, erbium, ytterbium, lutetium, and yttrium. The choice of lanthanide material may include a specific color of fluorescence emission. In some embodiments, multiple lanthanide materials may be used with different color emissions to enable multiplexing signals with a sensor array with colored pixels (e.g., a Red, Blue, and Green pixel array). For example, europium may be used for a red channel, while other lanthanides may be selected for green and blue emission. In one embodiment, the lanthanide material is embedded in or on a particle, such as a polystyrene particle. In some embodiments, different organic fluorescent dyes (e.g., Alexa Fluor, Cyanine, and the like) may be used for multiplexing colors and signal channels in the sample zone. The particles can be microparticles (particles less than about 1,000 micrometers in diameter, in some instances less than about 500 micrometers in diameter, in some instances less than 200, 150, or 100 micrometers in diameter) containing a luminescent or fluorescent lanthanide, wherein in some embodiments, the lanthanide is europium. In some embodiments, the lanthanide is a chelated europium. The microparticles, in some embodiments, have a core of a lanthanide material with a polymeric coating, such as a europium core with polystyrene coating. A binding partner for the analyte(s) of interest in the sample is/are attached to or associated with the outer surface of the microparticles. In some embodiments, the binding partner for the analyte(s) of interest is an antibody, a monoclonal antibody, or a polyclonal antibody. A skilled artisan will appreciate that other binding partners can be selected and can include complexes such as a biotin and streptavidin complex. Upon entering the label zone, the liquid sample hydrates, suspends, and mobilizes the dried microparticle-antibody conjugates and carries the conjugates together with the sample downstream on the test strip to the control or reference and/or test lines disposed on the immunoassay test strip. If an analyte of interest is present in the sample, it will bind to its respective conjugate as the specimen and microparticles flow from the label zone.

As the sample and microparticle-antibody conjugates continue to flow downstream on the immunoassay test strip, if the analyte of interest is present in the sample, the fluorescent microparticle-antibody conjugate, which is now bound with the antigen/analyte of interest, will bind to the specific binding member for the analyte of interest that is immobilized at the test line(s). In some embodiments, a single test line is present on the test strip. In some embodiments, at least two, or two or more test lines are present on the strip. By way of example, a test strip intended for detection and/or discrimination of influenza A and influenza B can include a first test line to detect influenza A and a second test line to detect influenza B.

Microparticle-antibody conjugates include microparticles coated with antibodies specific for influenza A and microparticles coated with antibodies specific for influenza B may be included in the label zone, and in some embodiments, downstream of the negative control line. A first test line for influenza A and a second test line for influenza B can be disposed downstream of the label zone. The first test line for influenza A comprises a monoclonal or polyclonal antibody to a determinant on the nucleoprotein of influenza A and the second test line for influenza B includes a monoclonal or polyclonal antibody to a determinant on the nucleoprotein of influenza B. If an antigen is present in the sample, a typical immunoassay sandwich will form on the respective test line that matches the antigen in the sample.

The microparticle-antibody conjugates that do not bind to the negative control line or to a test line continue to flow by capillary action downstream, and the remaining sample encounters the reference line, in some embodiments proceeding into the absorbent pad.

The immunoassay test device is intended for receiving a wide variety of samples, including biological samples from human bodily fluids, including but not limited to, nasal secretions, nasopharyngeal secretions, saliva, mucous, urine, vaginal secretions, fecal samples, blood, and the like.

The kit described herein, in some embodiments, is provided with a positive control swab or sample. In some embodiments, a negative control swab or sample is provided. For assays requiring an external positive and/or negative control, the user may be prompted to insert or apply a positive or negative control sample or swab.

An immunoassay band emits fluorescence light primarily from fluorophores bound to the target analyte, as they are fixed on the substrate by adherence to the immuno-proteins in the immunoassay strip (e.g., adsorption, chemi-sorption, immune-ligand, and the like). Accordingly, the presence of a red emission within the boundaries of the band is mostly attributable to the presence of the target analyte (e.g., presence of pathogenic antigens, and the like). However, the amount of red signal within the boundaries of the immunoassay band may include some background. To better assess the background signal (e.g., not originated by target analytes bound to the antibodies on the band), some sample cartridges may include a blank control area.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the clauses, such term is intended to be inclusive in a manner similar to the term "include" as "include" is interpreted when employed as a transitional word in a clause. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following clauses. For example, while operations are depicted in the drawings in a particular order, this should not be understood as requiring that such operations be performed in the particular order shown or in sequential order, or that all illustrated operations be performed, to achieve desirable results. The actions recited in the clauses can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products. Other variations are within the scope of the following clauses.

In one aspect, a method may be an operation, an instruction, or a function and vice versa. In one aspect, a clause may be amended to include some or all of the words (e.g., instructions, operations, functions, or components) recited in other one or more clauses, one or more words, one or more sentences, one or more phrases, one or more paragraphs, and/or one or more clauses.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system. Skilled artisans may implement the described functionality in varying ways for each particular application.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. No clause element is to be construed under the provisions of 35 U.S.C. § 112, sixth paragraph, unless the element is expressly recited using the phrase "means for" or, in the case of a method clause, the element is recited using the phrase "step for."

What is claimed is:

1. A method for determining presence or absence of an analyte of interest, comprising:
   receiving, in a client device, a radio signal from an image-capturing device when a test cartridge has been inserted in an enclosure of the image-capturing device, the test cartridge loaded with a sample;
   identifying the image-capturing device through a unique ID provided through the radio signal;
   pairing the image-capturing device and the client device;
   triggering multiple functions in the image-capturing device according to a schedule, the multiple functions comprising turning 'on' a light source in the image-capturing device;

receiving a data stream from the image-capturing device, the data stream comprising a first image of the test cartridge;

adjusting the first image of the test cartridge to improve an image quality and to reduce a size of the data stream, wherein adjusting the first image of the test cartridge comprises cropping the first image of the test cartridge;

determining the presence of a target analyte in the sample based on the first image of the test cartridge; and receiving, from the image-capturing device, a temperature value for a temperature inside an enclosure holding the test cartridge in the image-capturing device, and adjusting a performance characteristic of the sensor array in the image-capturing device.

2. A method for determining presence or absence of an analyte of interest, comprising:

receiving, in a client device, a radio signal from an image-capturing device when a test cartridge has been inserted in an enclosure of the image-capturing device, the test cartridge loaded with a sample;

identifying the image-capturing device through a unique ID provided through the radio signal;

pairing the image-capturing device and the client device;

triggering multiple functions in the image-capturing device according to a schedule, the multiple functions comprising turning 'on' a light source in the image-capturing device;

receiving a data stream from the image-capturing device, the data stream comprising a first image of the test cartridge; wherein receiving the data stream comprises receiving a testing metadata from the image-capturing device, the testing metadata comprising information in a fiduciary label of the test cartridge;

adjusting the first image of the test cartridge to improve an image quality and to reduce a size of the data stream, wherein adjusting the first image of the test cartridge comprises cropping the first image of the test cartridge; and determining the presence of a target analyte in the sample based on the first image of the test cartridge.

3. The method of claim 1, further comprising providing a power to the image-capturing device via a universal serial bus coupled to the client device.

4. A method for determining presence or absence of an analyte of interest, comprising:

receiving, in a client device, a radio signal from an image-capturing device when a test cartridge has been inserted in an enclosure of the image-capturing device, the test cartridge loaded with a sample;

identifying the image-capturing device through a unique ID provided through the radio signal;

pairing the image-capturing device and the client device;

triggering multiple functions in the image-capturing device according to a schedule, the multiple functions comprising turning 'on' a light source in the image-capturing device;

receiving a data stream from the image-capturing device, the data stream comprising a first image of the test cartridge, wherein the first image is collected at a first working distance;

adjusting the first image of the test cartridge to improve an image quality and to reduce a size of the data stream, wherein adjusting the first image of the test cartridge comprises cropping the first image of the test cartridge;

determining the presence of a target analyte in the sample based on the first image of the test cartridge;

receiving a second image in the data stream at a second working distance;

evaluating a quality of a measurement based on a comparison of the first image and the second image to determine which of the first and second images exhibits less lens aberration.

5. A method for capturing an image of a lateral flow assay from a sample in a test cartridge, comprising:

receiving, from a presence sensor, a signal indicative of a presence of the test cartridge within an enclosure;

providing, to a client device, a radio signal requesting a start of a measurement to identify the presence of a target analyte in the sample, the radio signal comprising a unique ID;

actuating a light shield to enclose a distal end of the test cartridge in response to insertion of the test cartridge into the enclosure and triggering the start of the measurement;

collecting a first image of the test cartridge from a sensor array; determining a quality of the measurement based on the first image;

adjusting the first image of the test cartridge to improve an image quality and to reduce a size of a data stream, wherein adjusting the first image of the test cartridge comprises cropping the first image of the test cartridge; and providing, to the client device, the data stream comprising a subject diagnostic based on a digital analysis of the image when the quality of the measurement is higher than a selected threshold.

6. The method of claim 5, further comprising turning 'on' a light source to illuminate the test cartridge for a selected time period, upon receipt of a trigger signal from the client device, and transmitting a light image to the client device, the light image collected from the sensor array when the light source is on.

7. The method of claim 5, wherein collecting the first image comprises collecting the image of the test cartridge while a light source is turned 'off'.

8. The method of claim 5, further comprising cropping the first image to capture a selected area of interest from the lateral flow assay.

9. The method of claim 1, wherein triggering multiple functions in the image-capturing device further comprises adjusting a performance setting in a sensor array in the image-capturing device, the performance setting comprising one of an exposure time, or a data transfer format.

10. The method of claim 2, wherein triggering multiple functions in the image-capturing device further comprises adjusting a performance setting in a sensor array in the image-capturing device, the performance setting comprising one of an exposure time, or a data transfer format.

11. The method of claim 2, further comprising providing a power to the image-capturing device via a universal serial bus coupled to the client device.

12. The method of claim 4, wherein triggering multiple functions in the image-capturing device further comprises adjusting a performance setting in a sensor array in the image-capturing device, the performance setting comprising one of an exposure time, or a data transfer format.

13. The method of claim 4, further comprising providing a power to the image-capturing device via a universal serial bus coupled to the client device.

* * * * *